US006486196B2

(12) United States Patent
Nanduri et al.

(10) Patent No.: US 6,486,196 B2
(45) Date of Patent: Nov. 26, 2002

(54) ANTICANCER COMPOUNDS: PROCESS FOR THEIR PREPARATION AND PHARMACEUTICAL COMPOSITIONS CONTAINING THEM

(75) Inventors: Srinivas Nanduri, Hyderabad (IN); Sairam Pothukuchi, Hyderabad (IN); Sriram Rajagopal, Hyderabad (IN); Venkateswarlu Akella, Hyderabad (IN); Sunilkumar Bhadramma Kochunarayana Pillai, Hyderabad (IN); Ranjan Chakrabarti, Hyderabad (IN)

(73) Assignee: Dr. Reddy's Research Foundation, Hyderabad (IN)

( * ) Notice: Subject to any disclaimer, the term of this patent is extended or adjusted under 35 U.S.C. 154(b) by 0 days.

(21) Appl. No.: 09/849,586

(22) Filed: May 4, 2001

(65) Prior Publication Data

US 2002/0016363 A1 Feb. 7, 2002

(30) Foreign Application Priority Data

May 5, 2000 (IN) ..................................... 354/MAS/2000

(51) Int. Cl.$^7$ ...................... A61K 31/335; A61K 31/34; A61K 31/42
(52) U.S. Cl. .................... 514/452; 514/374; 514/471; 514/473; 549/214; 549/313; 549/318; 548/239
(58) Field of Search .................... 549/214, 313, 549/318; 514/452, 471, 473, 374; 548/239

(56) References Cited

FOREIGN PATENT DOCUMENTS

| JP | 6388124 | 4/1988 |
| WO | 9101742 | 2/1991 |
| WO | 9617605 | 6/1996 |

OTHER PUBLICATIONS

Basak, A. et al. "Inhibition of Proprotein Convertases–1, –7 and Furin by Diterpines of *Andrographis paniculata* and Their Succinoyl Esters" Biochemistry Journal, vol., 338, p. 107–113, (1999).
Chang, R.S. et al. "Dehydroandrographolide Succinic Acid Monoester as an Inhibitor Against the Human Immunodeficiency Virus" Proc. Soc. Exp. Biol. Med., vol. 197, p. 59–66, (1991).
Matsuda, T. et al. "Cell Differentiation–Inducing Diterpenes from *Andrographis paniculata* Nees" Chem. Pharm. Bull. vol. 42 (6), p. 1216–1225, (1994).
Siripong, P. et al. "Cytotoxic Diterpenoid Constituents From *Andrographis paniculata* Nees Leaves" J. Sci. Soc. Thailand, vol. 18, p. 187–194, (1992).
Choudhury, B.R. et al. "In Vivo and In Vitro Effects of Kalmegh (*Andrographics paniculata*) Extract and Andrapgrapholide on Hepatic Microsomal . . . Enzymes" Planta Medica, vol. 53 (2), p. 135–140, (1987).

Puri, A. et al. "Immunostimulant Agents from *Andrographis paniculata*" Journal of Natural Product, vol. 56 (7), p. 995–999, (1993).
Rahman, N.N.N.A. et al. "Antimalarial Activity of Extracts of Malaysian Medicinal Plants" Journal of Ethanopharmacology, vol. 64, p. 249–254, (1999).
Misra, P. et al. Antimalarial Activity of *Andrographis paniculata* (Kalmegh) against *Plasmodium Berghei* NK 65 in *Mastomys natalensis*, Int. J. Pharmacog., vol. 30 (4), p. 263–274, (1992).
Long, D.W. "Antiinfammatory Agents from Traditional Chinese Drugs" Drugs of the Future, vol. 15 (8), p. 809–816, (1990).
"The Useful Plants of India" Ed. S.B. Ambasta, p. 39, (1992).
"Glossary of Indian Medicinal Plants " Ed. R.N. Chopra et al. p. 18, (1956).
Gupta, S. et al. "Antidiarrhoeal Activity of Diterpenes of *Andrographis paniculata* (Kal–Megh) Against *Escherichia coli* Enterotoxin in in vivo Models" Int. J. Crude Drug Res., vol. 28 (4), p. 273–283, (1990).
Medicinal & Aromatic Plants Abstracts, Wang, D.W. et al. Chinese Medical Journal, vol. 107 (6), p. 464–470, (1994).
Medicinal & Aromatic Plants Abstracts, Zhao, H. Y. et al. Chinese Medical Journal, vol. 104 (9), p. 770–775, (1991).
American Chemical Society, Meijer, L. Prog. Cell Cycle Research, vol. 1, p. 351–363, (1995).
Pharmaceutical Chemistry, K. Gorter, Rec. Trav. Chim. vol. 30, p. 151–160, (1911).
Cava, M.P. et al. "The Structure of Andrographolide" Tetrahedron, p. 397, (1962).

*Primary Examiner*—Amelia Owens
(74) *Attorney, Agent, or Firm*—Ladas & Parry

(57) ABSTRACT

The present invention relates to novel anticancer agents, their stereoisomers, their polymorphs, their pharmaceutically acceptable salts, and their pharmaceutically acceptable solvates. The present invention more particularly relates to novel derivatives of andrographolide, their stereoisomers, their polymorphs, their pharmaceutically acceptable salts, and their pharmaceutically acceptable solvates. The novel derivatives of andrographolide have the general formula (I).

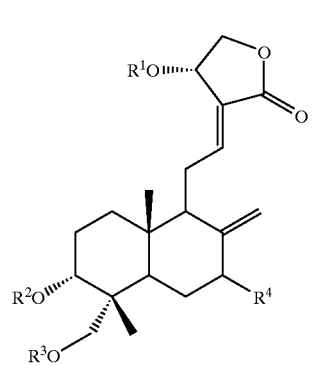

(I)

53 Claims, No Drawings

ANTICANCER COMPOUNDS: PROCESS FOR THEIR PREPARATION AND PHARMACEUTICAL COMPOSITIONS CONTAINING THEM

FIELD OF THE INVENTION

The present invention relates to novel anticancer agents, their stereoisomers, their polymorphs, their pharmaceutically acceptable salts, and their pharmaceutically acceptable solvates. The present invention more particularly relates to novel derivatives of andrographolide, their stereoisomers, their polymorphs, their pharmaceutically acceptable salts, and their pharmaceutically acceptable solvates. The novel derivatives of andrographolide have the general formula (I),

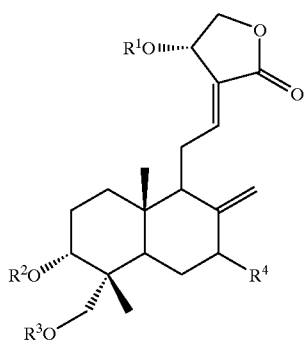

(I)

where $R^1$, $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, aralkanoyl, aralkenoyl, heteroaralkanoyl, heteroaralkenoyl, sulfonyl group or a group —(CO)—W—$R^5$ where W represents O, S or $NR^6$, wherein $R^6$ represents hydrogen or substituted or unsubstituted ($C_1$–$C_6$)alkyl group, $R^5$ represents substituted or unsubstituted groups selected from alkyl, aryl, aralkyl or aroyl or $OR^2$ and $OR^3$ together form a substituted or unsubstituted 6 or 7 membered cyclic structure containing carbon and oxygen atoms; $R^4$ represents hydrogen, halogen or $XR^7$ where X represents O, S, or NH and $R^7$ represents hydrogen or substituted or unsubstituted groups selected from alkyl, aryl, aralkyl, alkenoyl, alkanoyl, aroyl, heteroaroyl, aralkenoyl, aralkanoyl, sulfonyl groups or a group —(CO)—NH—$R^8$ where $R^8$ represents substituted or unsubstituted groups selected from alkyl, aryl, or aralkyl; with provisos that (i) $R^1$, $R^2$ and $R^3$ may be same except when they represent hydrogen or alkanoyl group and (ii) when $R^2$ and $R^3$ represent hydrogen, $R^1$ does not represent unsubstituted alkanoyl.

The andrographolide derivatives represented by general formula (I) as defined above and general formulas (X) and (XI) as defined below of the present invention are useful for treating cancer and other proliferative diseases including but not limited to herpes simplex virus types I and II (HSV I and HSV II) and human immunodeficiency (HIV). The compounds of the present invention are also useful in the treatment of psoriasis, restenosis, atherosclerosis and other cardiovascular disorders. The compounds of the present invention are also useful as antiviral, antimalarial, antibacterial, hepatoprotective, immunomodulating agents and for the treatment of metabolic disorders. The anticancer activity exhibited may be through cytotoxic activity, antiproliferation, cell cycle kinase inhibition or may be through cell differentiation.

The novel compounds of this invention are also useful for the treatment and/or prophylaxis of insulin resistance (type II diabetes), leptin resistance, impaired glucose tolerance, dyslipidemia, body weight reduction, disorders related to syndrome X such as hypertension, obesity, insulin resistance, coronary heart disease and other cardiovascular disorders.

The present invention also relates to pharmaceutical compositions containing compounds of general formula (I), formula (X), or formula (XI), or their stereoisomers, their polymorphs, their salts or their solvates or mixtures thereof.

The present invention also relates to a process for the preparation of the compounds of general formula (I), formula (X), and formula (XI), and their stereoisomers, their polymorphs, and their pharmaceutically acceptable salts, and their pharmaceutically acceptable solvates.

BACKGROUND OF THE INVENTION

The plant *andrographis paniculata* is extensively used in medicine as a bitter tonic, febrifuge and in bowel complaints (Glossary of Indian Medicinal Plants., Ed. R. N. Chopra, S. L. Nayar, I. C. Chopra, p18, 1996. The useful plants of India, Ed. By S. B. Ambasta, p39, 1992). The plant is useful in the treatment of bacterial infections (Int. J. Crude Drug Res. 1990, 28(4), p273–283; Drugs of the Future. 1990, 15(8) p809–816). It is reported to possess antimalarial (Int. J. Pharmacognosy, 1992, 30(4), p263–274; J. Ethnopharmacol., 1999, 64(3), p249–254) and immunostimulant activity (J. Nat. Prod., 1993, 56(7), p995–999). The plant has also been shown to be antithrombotic (Chinese Medical Journal 1991, 104(9), p770–775) and inhibit stenosis and restenosis after angioplasty in the rat (Chinese Medical Journal, 1994, 107(6), p464–470). It is also known that the plant extract and its constituents exhibit promising hepatoprotective activity (Planta Medica, 1987, 53(2), p135–140). Significant attention has been paid by several research groups on *A. paniculata* in recent years due to its cytotoxic, antitumorogenic, cell differentiation inducing activities and anti-HIV activities.

Andrographolide having the formula (II),

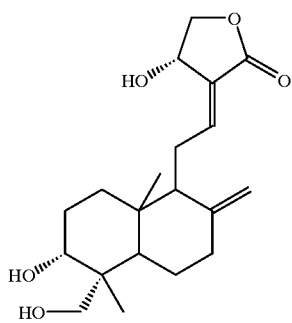

II the major constituent of the plant *A. paniculata* was first isolated by Gorter (Rec. trav. chim., 1911, 30, p151–160).

III

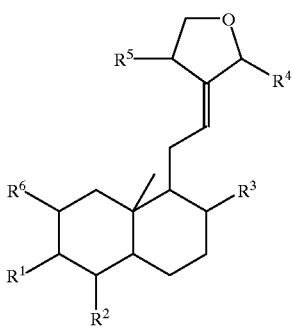

The extracts of the dried plant, which contains compounds of formula (III), have been assayed for the ability to decrease expression and phosphorylation of $p34^{cdc2}$ kinase, cyclin B and c-Mos for treating or preventing pathogenecity of diseases such as AIDS, Alzheimer's disease and hepatitis (WO 96/17605).

Cell cycle kinases are naturally occurring enzymes involved in regulation of the cell cycle (*Progress in Cell Cycle Research*, 1995, 1, p351–363). Typical enzymes include the cyclin-dependent kinases (cdk) cdk1, cdk2, cdk4, cdk5, cdk6 and wee-1 kinase. Increased activity or temporarily abnormal activation of these kinases has been shown to result in development of tumors and other proliferative disorders such as restenosis. Compounds that inhibit cdks, either by blocking the interaction between a cyclin and its kinase partner or by binding to and inactivating the kinase, cause inhibition of cell proliferation and are thus useful for treating tumors or other abnormally proliferating cells.

The extract of *A. paniculata* was found to show significant cytotoxic activity against KB and P388 cells. Interestingly, Andrographolide of the formula II, has been shown for the first time to have potent cytotoxic activity against KB as well as P388 lymphocytic leukemia, where as 14-deoxy-11,12-didehydroandrographolide and neoandrographolide having the formulae IV & V (IV)

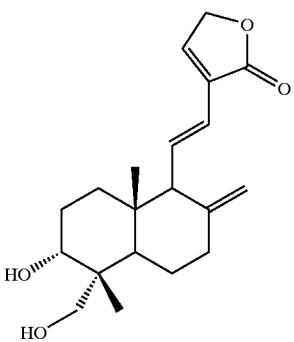

-continued (V)

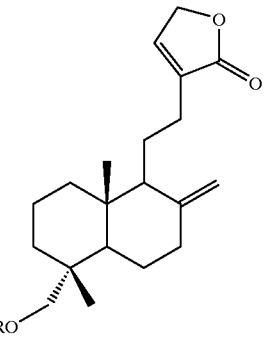

where R represents β-D-glucose moiety, have shown no cytotoxic activity in tumor cell lines (*J. Sci. Soc. Thailand*, 1992, 18, p187–194).

The methanolic extract of the aerial parts of *A. paniculata* Nees showed potent cell differentiation inducing activity on mouse myeloid leukemia (M1) cells (*Chem. Pharm. Bull.* 1994, 42(6) 1216–1225).

Japanese patent application JP 63-88124, discloses a mixture of at least two compounds of formula VIa, VIb, VIa

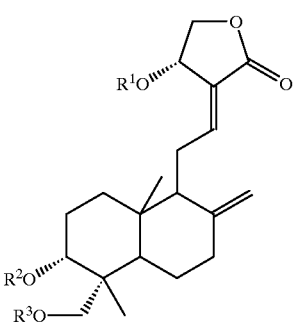

VIb

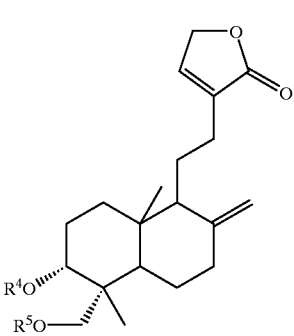

where $R^1$, $R^2$, $R^3$, $R^4$ and $R^5$ represent hydrogen or lower alkanoyl group and their activity as antitumorogenic agents.

DASM (dehydroandrographolide succinic acid monoester) prepared from andrographolide of the formula II is found to be inhibiting HIV virus and nontoxic to the H9 cell at the concentrations of 50–200 μg/ml and was inhibitory to HIV-1 (EIB) at the minimal concentration of 1.6–3.1 μg/ml (*Proc. Soc. Exp. Biol. Med.*, 1991, 197, p59–66).

The plant *Andrographis paniculata* is also reported to inhibit proprotein convertases-1,-7 and furin possibly by suppressing the proteolytic cleavage of envelops glycoprotein gp 160 of HIV, which is known to be PC-mediated, particularly by furin and PC (*Biochem. J*, 1999, 338, 107–113)

In International patent application WO 91/01742, compositions containing one or more ingredients obtained from the plants *Valeariana officinalis* and/or *A. paniculata* were disclosed to have antiviral, antineoplastic, antibacterial and immunomodulatory activity.

Although several novel andrographolide derivatives have been prepared, screened and reported in the above said prior-art literature for their anticancer activity, they are not showing interesting activity.

OBJECTIVE OF THE INVENTION

With an objective of preparing novel andrographolide derivatives useful for treating cancer, infections and diseases caused by HSV, HIV, psoriasis, restenosis, atherosclerosis, cardiovascular disorders, also useful as antiviral, antimalarial, antibacterial, hepatoprotective, immunomodulating agents and for treatment of metabolic disorders, which are potent at lower doses and having better efficacy with lower toxicity, we focussed our research efforts in preparing the novel andrographolide derivatives of the formula (I) as defined above.

The main objective of the present invention is, therefore, to provide novel andrographolide derivatives of the formula (I), formula (X), formula (XI), their stereoisomers, their polymorphs, their pharmaceutically acceptable salts, their pharmaceutically acceptable solvates and compositions containing them or their mixtures.

Another objective of the present invention is to provide pharmaceutical compositions containing compounds of formula (I), formula (X), formula (XI), their stereoisomers, their polymorphs, their pharmaceutically acceptable salts, or their pharmaceutically acceptable solvates or their mixtures in combination with suitable carriers, solvents, diluents and other media normally employed in preparing such compositions.

Still another objective of the present invention is to provide pharmaceutical compositions containing compounds of formula (I), formula (X), formula (XI), their stereoisomers, their polymorphs, their pharmaceutically acceptable salts, or their pharmaceutically acceptable solvates, or their mixtures in combination with one or more pharmaceutically acceptable active compounds with suitable carriers, solvents, diluents and other media normally employed in preparing such compositions.

Still another objective of the present invention is to provide a process for the preparation of novel andrographolide derivatives of the formula (I), formula (X), formula (XI), their stereoisomers, their polymorphs, their pharmaceutically acceptable salts, and their pharmaceutically acceptable solvates and pharmaceutical compositions containing them or their mixtures having enhanced activity with little or no toxic effect or reduced toxic effect.

DETAILED DESCRIPTION OF THE INVENTION

Accordingly, the novel derivatives of andrographolide of the present invention have the general formula (I)

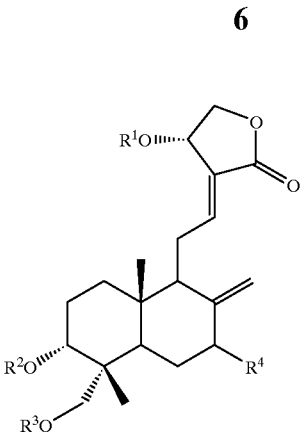

(I)

where $R^1$, $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, aralkanoyl, aralkenoyl, heteroaralkanoyl, heteroaralkenoyl, sulfonyl group or a group —(CO)—W—$R^5$ where W represents O, S or $NR^6$, wherein $R^6$ represents hydrogen or substituted or unsubstituted $(C_1-C_6)$alkyl group, $R^5$ represents substituted or unsubstituted groups selected from alkyl, aryl, aralkyl or aroyl or $OR^2$ and $OR^3$ together form a substituted or unsubstituted 6 or 7 membered cyclic structure containing carbon and oxygen atoms; $R^4$ represents hydrogen, halogen or $XR^7$ where X represents O, S, or NH and $R^7$ represents hydrogen or substituted or unsubstituted groups selected from alkyl, aryl, aralkyl, alkenoyl, alkanoyl, aroyl, heteroaroyl, aralkenoyl, aralkanoyl, sulfonyl groups or a group —(CO)—NH—$R^8$ where $R^8$ represents substituted or unsubstituted groups selected from alkyl, aryl, or aralkyl; with provisos that (i) $R^1$, $R^2$ and $R^3$ may be same except when they represent hydrogen or alkanoyl group and (ii) when $R^2$ and $R^3$ represent hydrogen, $R^1$ does not represent unsubstituted alkanoyl; their stereoisomers, their polymorphs, their pharmaceutically acceptable salts and their pharmaceutically acceptable solvates.

Suitable groups represented by $R^1$, $R^2$ and $R^3$ include hydrogen, substituted or unsubstituted, linear or branched $(C_1-C_8)$ alkyl group such as methyl, ethyl, n-propyl, isopropyl and the like; aryl group such as phenyl, naphthyl and the like, the aryl group may be substituted; heteroaryl group such as pyridyl, furyl, thiophenyl and the like, the heteroaryl group may be substituted; aralkyl such as benzyl, phenethyl and the like, the aralkyl group may be substituted; heteroaralkyl group such as pyridylmethyl, pyridylethyl, furanmethyl, furanethyl and the like, the heteroaralkyl group may be substituted; $(C_2-C_8)$ alkanoyl group such as ethanoyl, propanoyl, butanoyl and the like, the $(C_2-C_8)$ alkanoyl group may be substituted; $(C_3-C_8)$ alkenoyl group such as propenoyl, butenoyl, pentenoyl and the like, $(C_3-C_8)$ alkenoyl group may be substituted; aroyl group such as benzoyl and the like, the aroyl group may be substituted; heteroaroyl group such as pyridyl carbonyl, furyl carbonyl and the like; the heteroaroyl group may be substituted; aralkenoyl group such as phenylpropenoyl, phenylbutenoyl, phenylpentenoyl and the like, the aralkenoyl group may be substituted; aralkanoyl group such as phenylpropanoyl, phenylbutanoyl, phenylpentanoyl and the like, the aralkanoyl group may be substituted; heteroaralkanoyl group such as pyridylethanoyl, pyridylpropanoyl, thiopheneethanoyl, thiophenepropanoyl and the like, the heteroaralkanoyl group may be substituted; heteroaralkenoyl group such as pyridylethenoyl, pyridylpropenoyl, thiopheneethenoyl, thiophenepropenoyl and the like, the heteroaralkenoyl group may be substituted; sulfonyl group such as methanesulfonyl, benzenesulfonyl, p-toluenesulfonyl and the like, the sulfonyl group may be substituted.

Suitable cyclic structures formed by $OR^2$ and $OR^3$ may be selected from $—O—(CR^9R^{10})_m—O—$ where $R^9$ and $R^{10}$ may be same or different and independently represent hydrogen, unsubstituted or substituted groups selected from $(C_1-C_6)$ alkyl such as methyl, ethyl, n-propyl and the like; aryl group such as phenyl, naphthyl and the like, the aryl group may be substituted; heteroaryl group such as pyridyl, furyl, thiophenyl, pyrrolyl and the like; the heteroaryl group may be substituted or $R^9$ and $R^{10}$ together represent C=O; m represents an integer 1 or 2. The substituents on $R^9$ and $R^{10}$ include hydroxy, halogen such as fluorine, chlorine, bromine and the like; nitro, cyano or amino, $(C_1-C_6)$alkyl, $(C_1-C_6)$alkoxy, aryl or aroyl groups.

Suitable groups represented by $R^4$ include hydrogen, halogen such as fluorine, chlorine, bromine and the like; or $XR^7$ where $R^7$ represents hydrogen or linear or branched $(C_1-C_8)$ alkyl group such as methyl, ethyl, n-propyl, iso-propyl and the like, the alkyl group may be substituted; aryl group such as phenyl, naphthyl and the like, the aryl group may be substituted; aralkyl such as benzyl, phenethyl and the like, the aralkyl group may be substituted; $(C_3-C_8)$ alkenoyl group such as propenoyl, butenoyl, pentenoyl and the like, the alkenoyl group may be substituted; $(C_2-C_8)$ alkanoyl group such as ethanoyl, propanoyl, butanoyl and the like, the alkanoyl group may be substituted; aroyl group such as benzoyl and the like, the aroyl group may be substituted; heteroaroyl group such as pyridyl carbonyl, furyl carbonyl and the like, the heteroaroyl group may be substituted; aralkenoyl group such as phenylpropenoyl, phenylbutenoyl, phenylpentenoyl and the like, the aralkenoyl group may be substituted; aralkanoyl group such as phenylpropanoyl, phenylbutanoyl, phenylpentanoyl and the like, the aralkanoyl group may be substituted; sulfonyl group such as methanesulfonyl, benzenesulfonyl, p-toluenesulfonyl and the like, the sulfonyl group may be substituted or a group $—(CO)—NH—R^8$ where $R^8$ represents linear or branched $(C_1-C_8)$ alkyl group such as methyl, ethyl, n-propyl, iso-propyl and the like, $(C_1-C_8)$alkyl group may be substituted; aryl group such as phenyl, naphthyl and the like, the aryl group may be substituted; or aralkyl such as benzyl, phenethyl and the like, the aralkyl group may be substituted.

Suitable groups represented by $R^5$ include $(C_1-C_6)$alkyl such as methyl, ethyl, n-propyl and the like, the $(C_1-C_6)$ alkyl group may be substituted; aryl group such as phenyl, naphthyl and the like, the aryl group may be substituted; aralkyl such as benzyl, phenethyl and the like, the aralkyl group may be substituted; or aroyl group such as benzoyl and the like, the aroyl group may be substituted. The substituents on the alkyl group, aromatic moiety of the aryl group, aralkyl group or aroyl group include halogen atom such as fluorine, chlorine and bromine; amino group, cyano, hydroxy, nitro, trifluoroethyl, $(C_1-C_6)$ alkyl, or $(C_1-C_6)$ alkoxy.

Suitable groups represented by $R^6$ include hydrogen, or substituted or unsubstituted $(C_1-C_6)$ alkyl such as methyl, ethyl, n-propyl and the like. The substituents on the alkyl group include halogen atom such as fluorine, chlorine and bromine; amino group, cyano, hydroxy, nitro, trifluoroethyl, $(C_1-C_6)$ alkyl, or $(C_1-C_6)$ alkoxy.

The suitable substituents on $R^1$, $R^2$, R $R^7$ and $R^8$ may be selected from cyano, hydroxy, nitro, thio, halogen atom such as fluorine, chlorine, bromine and the like; or substituted or unsubstituted groups selected from linear or branched $(C_1-C_8)$ alkyl group such as methyl, ethyl, n-propyl, iso-propyl and the like; amino, mono or disubstituted amino group; alkanoyl group such as ethanoyl, propanoyl, butanoyl and the like; thio$(C_1-C_8)$alkyl such as thiomethyl, thioethyl, thiopropyl and the like; $(C_1-C_6)$alkoxy group such as methoxy, ethoxy, propyloxy, butyloxy and the like; aroyl group such as benzoyl and the like; acyloxy group such as acetyloxy, propanoyloxy, butanoyloxy and the like; aryl group such as phenyl, naphthyl and the like, the aryl group may be mono or disubstituted; heteroaryl group such as pyridyl, furyl, thienyl and the like; acylamino groups such as $CH_3CONH$, $C_2H_5CONH$, $C_3H_7CONH$, $C_4H_9CONH$ and $C_6H_5CONH$; aralkylamino group such as $C_6H_5CH_2NH$, $C_6H_5CH_2CH_2NH$, $C_6H_5CH_2NCH_3$ and the like; alkoxycarbonylamino group such as $C_4H_9OCONH$, $C_2H_5OCONH$, $CH_3OCONH$ and the like; aryloxycarbonylamino group such as $C_6H_5OCONH$, $C_6H_5OCONCH_3$, $C_6H_5OCONC_2H_5$, $C_6H_4(CH_3)OCONH$, $C_6H_4(OCH_3)OCONH$, and the like; aralkoxycarbonylamino group such as $C_6H_5CH_2OCONH$, $C_6H_5CH_2CH_2OCONH$, $C_6H_5CH_2OCON(CH_3)$, $C_6H_5CH_2OCON(C_2H_5)$, $C_6H_4(CH_3)CH_2OCONH$, $C_6H_4(OCH_3)CH_2OCONH$ and the like; $(C_1-C_8)$alkylthio group such as methylthio, ethylthio, propylthio and the like; heteroarylthio group such as pyridylthio, furylthio, thiophenylthio, benzothiazolethio, purinethio, benzimidazolethio, pyrimidinethio and the like; acylthio group such as acetylthio, propanoylthio, butanoylthio and the like; aralkylthio group such as benzylthio, phenylethylthio, phenylpropylthio and the like; arylthio group such as phenylthio, napthylthio and the like; $(C_1-C_8)$ alkylseleno such as methylseleno, ethylseleno, propylseleno, iso-propylseleno and the like; acylseleno such as acetylseleno, propionylseleno and the like; aralkylseleno such as benzylseleno, phenylethylseleno, phenylpropylseleno and the like; arylseleno such as phenylseleno, napthylseleno and the like or COOR, where R represents hydrogen or $(C_1-C_6)$ alkyl groups. The substituents are selected from halogen, hydroxy, nitro, cyano, amino, $(C_1-C_6)$alkyl, aryl or $(C_1-C_6)$alkoxy groups.

When the groups $R^1$, $R^2$, $R^3$, $R^5$, $R^7$ and $R^8$ represent disubstituted aryl, the two substituents on the adjacent carbon atoms form a linking group such as $—X—CH_2—Y—$, $—X—CH_2—CH_2—Y—$, where X and Y may be same or different and independently represent O, NH, S or $CH_2$.

When the groups represented by $R^1$, $R^2$, $R^3$, $R^5$, $R^7$ and $R^8$ are multi substituted, the substituents present on the two adjacent carbons may form a linking group $—X—(CR^{11}R^{12})_n—Y—$ where $R^{11}$ and $R^{12}$ represent $(C_1-C_8)$ alkyl such as methyl, ethyl and the like, X and Y may be same or different and independently represent $CH_2$, O, S, NH; and n=1 or 2.

Pharmaceutically acceptable salts forming part of this invention include salts derived from inorganic bases such as Li, Na, K, Ca, Mg, Fe, Cu, Zn, Mn; salts of organic bases such as N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine, and the like; chiral bases like alkylphenylamine, glycinol, phenyl glycinol and the like, salts of natural amino acids such as glycine, alanine, valine, leucine, isoleucine, norleucine, tyrosine, cystine, cysteine, methionine, proline, hydroxy proline, histidine, ornithine, lysine, arginine, serine, threonine, and phenylalanine; unnatural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprise other solvents of crystallization such as alcohols.

Particularly useful compounds according to present invention include:

3,19-Isopropylidene andrographolide;

3,19-Benzylidene andrographolide;

3,19-(1-Phenylethylidene)andrographolide;

3,19-Isopropylidene-14-(N-Boc methionyl) andrographolide;

14-Acetyl 3,19-methylenedioxy andrographolide;

14-Acetyl 3,19-O-cyclic carbonyl andrographolide;

14-Acetyl andrographolide;

14-Chloroacetyl andrographolide;

14-(Phenylcarbamoyl)andrographolide;

14-(N-Isopropyl carbamoyl)andrographolide;

14-Cinnamoyl andrographolide;

14-Isopropanoyl andrographolide;

14-Pivaloyl andrographolide;

14-Benzoyl andrographolide;

14-Benzyl andrographolide;

3,19-Diacetyl-14-(2'-acetyl-3'-acetamido 3'-phenyl) propionyl andrographolide;

3,19-Diacetyl-14-[4'S,5'R-(N-t-Butoxycarbonyl)-2',2'-dimethyl-4'-phenyl-5'-oxazolidine]carbonyl andrographolide;

3,19-Diacetyl-14-(2'hydroxy-3'-benzoylamino 3'-phenyl) propionyl andrographolide;

3,19-Diacetyl-14-(2'hydroxy-3-N-Boc amino-3'-phenyl) propionyl andrographolide;

14-(N-Boc-glycinyl)-3,19-dipropionyl andrographolide;

14-(N-Boc-glycinyl)-3,19-diacetyl andrographolide;

14-(N-Acetylglycinyl)-3,19-diacetyl andrographolide;

14-(N-Benzoylglycinyl)-3,19-diacetyl andrographolide;

3,19-Diacetyl-14-O-ethyl andrographolide;

3,19-Diacetyl-14-O-methyl andrographolide;

3,19-Diacetyl-14-(3,4-dimethoxycinnamoyl) andrographolide;

14-(3,4-dimethoxy)cinnamoyl-3,19-dipropionyl-andrographolide;

3-Acetyl andrographolide;

3,14-Diacetyl andrographolide;

3,14,19,7-Tetra acetyl andrographolide;

3,19-Isopropylidene-14-acetyl andrographolide;

14-Chloroacetyl-3,19-isopropylidene andrographolide;

14-Carbamoyl-3,19-isopropylidene andrographolide;

3,19-Isopropylidene-14-(N-isopropyl)carbamoyl andrographolide;

14-[4'S,5R-(N-t-butoxycarbonyl-2',2'-dimethyl-4'-phenyl-5'-oxazolidine]carbonyl 3,19-isopropylidene andrographolide;

14-[4'S,5'R-(N-t-butoxycarbonyl-2',2'-dimethyl-4'-phenyl-5'-oxazolidine]carbonyl andrographolide;

3,19-Isopropylidene-14-(N-Boc-glycinyl) andrographolide;

14-(N-Boc-glycinyl)andrographolide;

14-O-Ethyl-3,19-isopropylidene andrographolide;

14-O-Ethyl andrographolide;

14-O-Methyl-3,19-isopropylidene andrographolide;

14-O-Methyl andrographolide;

14-(3,4-Dimethoxy)cinnamoyl andrographolide;

19-Trityl andrographolide;

3-Acetyl-19-trityl andrographolide;

3,14-Diacetyl-19-trityl andrographolide and 7-Hydroxy-3,14,19-triacetyl andrographolide.

The present invention also provides a process for the preparation of novel andrographolide of the general formula (I), where $R^1$, $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, aralkanoyl, aralkenoyl, heteroaralkanoyl, heteroalkenoyl, sulfonyl group or a group —(CO)—W—$R^5$ where W represents O, S or $NR^6$, wherein $R^6$ represents hydrogen or substituted or unsubstituted ($C_1$–$C_6$)alkyl group, $R^5$ represents substituted or unsubstituted groups selected from alkyl, aryl, aralkyl or aroyl or $OR^2$ and $OR^3$ together form a substituted or unsubstituted 6 or 7 membered cyclic structure containing carbon and oxygen atoms and $R^4$ represents hydrogen; with provisos that (i) $R^1$, $R^2$ and $R^3$ may be same except when they represent hydrogen or alkanoyl group, (ii) when $R^2$ and $R^3$ represent hydrogen, $R^1$ does not represent unsubstituted alkanoyl; their stereoisomers, their polymorphs, their pharmaceutically acceptable salts and their pharmaceutically acceptable solvates, which comprises: reacting the compound of formula (VII)

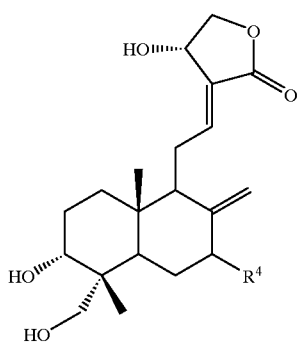

(VII)

with $R^1$—L, $R^2$—L and $R^3$—L, where $R^1$, $R^2$ and $R^3$ are as defined above and L represents hydroxy or a leaving group such as halogen atom like fluorine, chlorine, bromine or iodine; p-toluenesulfonate, methanesulfonate, trifluoromethanesulfonate and the like; or an alkanoate such as acetate, propanoate, butanoate and the like, to produce a compound of formula (I), where all symbols are as defined earlier and $R^4$ represents hydrogen.

The reaction of a compound of formula (VII) with $R^1$—L, $R^2$—L and $R^3$—L, to produce a compound of formula (1) may be carried out in the presence of dicyclohexylcarbodiimide (DCC), diethyl azadicarboxylate (DEAD), diisopropyl azadicarboxylate (DIAD) and the like. The reaction may be carried out in the absence or presence of a base selected from triethylamine, pyridine, dimethyl aminopyridine and the like. The reaction may be carried out in the presence of solvents such as dichloromethane, chloroform, $C_6H_6$, dimethyl sulfoxide, methanol, ethanol and the like or mixtures thereof. The reaction may be carried out at a temperature in the range of 0° C. to 200° C., preferably at a temperature in the range of 20° C. to 160° C. and the reaction time may range from 2 to 12 h, preferably from 2 to 10 h.

In another embodiment of the present invention the compounds of formula (I) may also be prepared by a process, which comprises:

(i) protecting the hydroxy groups present on carbons 3 or 19 or 3 and 19 together in the compound of formula (VII) with suitable protecting groups using conventional methods to produce a compound of formula (VIII), (VIII)

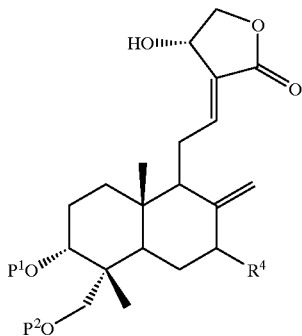

where $R^4$ represents hydrogen; $P^1$ and $P^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene, carbonate and the like, (ii) reacting the compound of formula (VIII) defined above with a compound of formula (IX)

$R^1$—L        (IX)

where $R^1$ and L have the meanings given above to produce a compound of formula (X), (X)

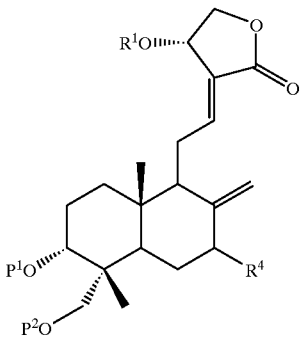

where $R^1$, $R^4$, $P^1$ and $P^2$ are as defined above, (iii) deprotecting the compound of formula (X) by conventional methods to produce a compound of formula (XI), (XI)

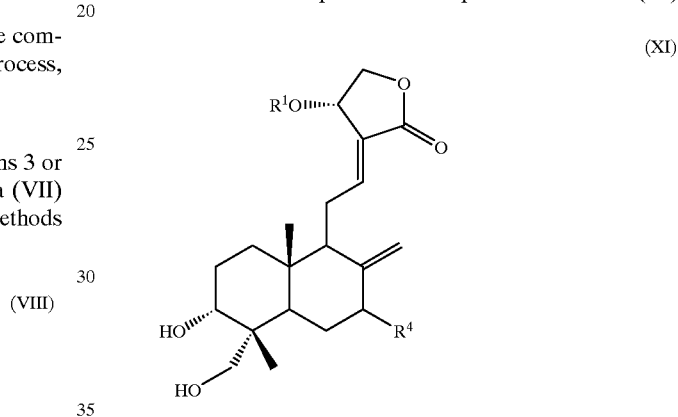

where $R^1$ and $R^4$ have the meanings given above, (iv) reacting the compound of formula (XI) where $R^1$ has the meaning given above with $R^2$—L and/or $R^3$—L, where $R^2$ and $R^3$ are as defined above to produce a compound of formula (I), and if desired, (v) converting the compound of formula (I) into their stereoisomers, pharmaceutical salts by conventional methods.

The protection of a compound of formula (VII) may be carried out using trityl chloride, t-butyldimethylsilyl chloride, pivaloyl chloride, dimethylsulfoxide, acetone, 2,2-dimethoxy propane, trimethyl ortho acetate, benzaldehyde, p-methoxy benzaldehyde and the like. The reaction may be carried out in the presence of a suitable catalyst such as $SOCl_2$, $H_2SO_4$, $HClO_4$, pyridinium p-toluene sulphonate, pyridine, p-toluene sulfonic acid, dimethyl aminopyridine, and the like. The reaction may be carried out in the absence or presence of suitable solvent such as benzene, DMF, DMSO, acetonitrile, DCM, and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h.

The reaction of a compound of formula (VIII) with a compound of formula (IX) to produce a compound of formula (X) may be carried out in the presence of dicyclohexylcarbodiimide (DCC), diethyl azadicarboxylate (DEAD), diisopropyl azadicarboxylate (DLAD) and the like. The reaction may be carried out in the absence or presence of a base selected from triethylamine, pyridine, dimethyl aminopyridine and the like. The reaction may be carried out in the presence of solvents such as dichloromethane, chloroform, C₆H₆, dimethyl sulfoxide, methanol, ethanol and the like or mixtures thereof. The reaction may be carried out at a temperature in the range of 0° C. to 200° C., preferably at a temperature in the range of 20° C. to 160° C. and the reaction time may range from 2 to 12 h, preferably from 2 to 10 h.

The deprotection of a compound of formula (X) to produce a compound of formula (XI) may be carried out using deprotecting agent such as acetic acid, hydrochloric acid, formic acid, trifluoroacetic acid and the like. The reaction may be carried out in the presence of a suitable solvent such as water, THF, dioxane, DCM, CHCl₃, methanol and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h.

The reaction of compound of formula (XI) with R²—L and/or R³—L, to produce a compound of formula (I) may be carried out in the presence of dicyclohexylcarbodiimide (DCC), diethyl azadicarboxylate (DEAD), diisopropyl azadicarboxylate (DIAD) and the like. The reaction may be carried out in the absence or presence of a base selected from triethylamine, pyridine, dimethyl aminopyridine and the like. The reaction may be carried out in the presence of solvents such as dichloromethane, chloroform, C₆H₆, dimethyl sulfoxide, methanol, ethanol and the like or mixtures thereof. The reaction may be carried out at a temperature in the range of 0° C. to 200° C., preferably at a temperature in the range of 20° C. to 160° C. and the reaction time may range from 2 to 12 h, preferably from 2 to 10 h.

In another embodiment of the invention there is provided a process for the preparation of the compound of formula (I) where R⁴ represents XR⁷ where R⁷ and other symbols are as defined earlier, their stereoisomers, their polymorphs, their pharmaceutically acceptable salts and their pharmaceutically acceptable solvates, which comprises:

(i) converting the compound of formula (I) where R⁴ represents hydrogen and all other symbols are as defined earlier to produce a compound of formula (XII),

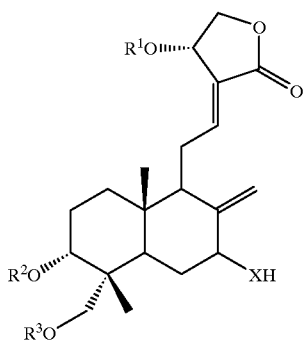

(XII)

where all the symbols are as defined above, the compound of formula (XII) represents a compound of formula (I) when X represents O, (ii) reacting the compound of formula (XII) with R⁷—L where R⁷ is as defined earlier, to produce a compound of formula (I).

Conversion of the compound of formula (I) to produce a compound of formula (XII) may be carried out in the presence of reagents such as SeO₂, t-BuO₂H, H₂O₂ and the like. The reaction may be carried out in the presence of solvents such as DCM, CHCl₃, benzene, THF, dioxane, DMF, methanol, ethanol and the like or mixtures thereof. The temperature and duration of the reaction may be maintained in the range of 0 to 30° C. and 3 to 48 h respectively.

The reaction of compound of formula (XII) with R⁷—L to produce a compound of formula (I) may be carried out in the presence of dicyclohexylcarbodiimide (DCC), diethyl azadicarboxylate (DEAD), diisopropyl azadicarboxylate (DIAD) and the like. The reaction may be carried out in the absence or presence of a base selected from triethylamine, pyridine, dimethyl aminopyridine and the like. The reaction may be carried out in the presence of solvents such as dichloromethane, chloroform, C₆H₆, dimethyl sulfoxide, methanol, ethanol and the like or mixtures thereof. The reaction may be carried out at a temperature in the range of 0° C. to 200° C., preferably at a temperature in the range of 20° C. to 160° C. and the reaction time may range from 2 to 12 h, preferably from 2 to 10 h.

In another embodiment of the invention there is provided a process for the preparation of the compound of formula (I) where R⁴ represents halogen and other symbols are as defined earlier, their stereoisomers, their polymorphs, their pharmaceutically acceptable salts and their pharmaceutically acceptable solvates, which comprises:

(i) converting the compound of formula (I) where R⁴ represents hydrogen and all other symbols are as defined earlier to produce a compound of formula (XII),

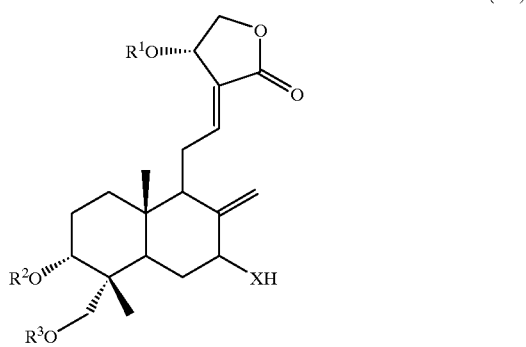

(XII)

where all the symbols are as defined above, the compound of formula (XII) represents a compound of formula (I) when X represents O, (ii) converting the compound of formula (XII) to a compound of formula (I), where R⁴ represents halogen atom such as fluorine, chlorine, bromine or iodine.

Conversion of the compound of formula (I) to produce a compound of formula (XII) may be carried out in the presence of reagents such as SeO₂, t-BuO₂H, H₂O₂ and the like. The reaction may be carried out in the presence of solvents such as DCM, CHCl₃, benzene, THF, dioxane, DMF, methanol, ethanol and the like or mixtures thereof. The temperature and duration of the reaction may be maintained in the range of 0 to 30° C. and 3 to 48 h respectively.

The conversion of compound of formula (XII) to compound of formula (I) may be carried out using halogenating agents such as thionyl chloride, thionyl bromide, phosphonyl chloride, PCl₅, PBr₃, bromine trifluoride, N-bromosuccinimide-hydrogen fluoride (NBS-HF), cobalt (III) fluoride, lithium fluoride, potassium fluoride, sodium fluoride, cesium fluoride, potassium iodide, sodium iodide, iodine, iodine cerium (IV) ammonium nitrate or R⁷—L where R⁷ and L are as defined above. The reaction may be carried out in the presence of solvents such as ether, dichloromethane, chloroform, DMF, DMSO and the like. The reaction may be carried out in the range of −40° C. to 160° C. The duration of the reaction may range from 1 to 6 h.

In another embodiment of the invention there is provided a process for the p reparation of the compound of formula (I) where $R^4$ represents halogen and other symbols are as defined earlier, their stereoisomers, their polymorphs, their pharmaceutically acceptable salts and their pharmaceutically acceptable solvates, which comprises: reacting the compound of formula (I) where $R^4$ represents hydrogen and all other symbols are as defined earlier with suitable halogenating agent to produce a compound of formula (I), where $R^4$ represents halogen atom such as fluorine, chlorine, bromine or iodine.

The reaction of compound of formula (I) where $R^4$ represents hydrogen with halogenating agents, to produce a compound of formula (I) where $R^4$ represents halogen may be carried out in the presence of reagents such as bromine trifluoride, N-bromosuccinimide-hydrogen fluoride (NBS-HF), cobalt (III) fluoride, lithium fluoride, potassium fluoride, sodium fluoride, cesium fluoride, potassium iodide, sodium iodide, iodine, iodine cerium (IV) ammonium nitrate, N-bromosucinimide, (NBS), N-chlorosucinimide (NCS), N-iodosucinimide (NIS), bromine, chlorine, $POCl_3$, $PCl_3$, $PBr_3$ or $SOCl_2$. The reaction may be carried out in the presence of solvents such as DCM, $CHCl_3$, benzene, THF, dioxane, DMF, methanol, ethanol and the like or mixtures thereof. The temperature and duration of the reaction may be maintained in the range of −80 to 32° C. and 3 to 48 h respectively.

In another embodiment of the present invention there is provided a novel intermediate of formula (X)

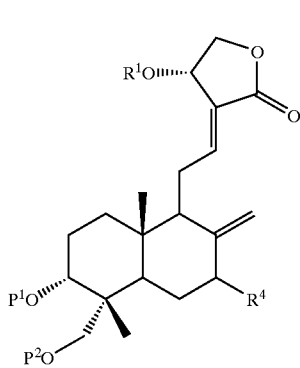

(X)

where $R^1$ represents hydrogen or substituted or unsubstituted groups selected from alkyl, aryl, heteroaryl, aralkyl, heteroaralkyl, alkanoyl, alkenoyl, aroyl, aralkanoyl, aralkenoyl, heteroaroyl, heteroaralkanoyl, heteroaralkenoyl, sulfonyl groups or a group —(CO)—W—$R^5$ where W represents O, S or $NR^6$, wherein $R^6$ represents hydrogen or substituted or unsubstituted ($C_1$-$C_6$)alkyl group, $R^5$ represents substituted or unsubstituted groups selected from alkyl, aryl, aralkyl or aroyl; $R^4$ represents hydrogen; $P^1$ and $P^2$ may be same or different and independently represent trityl, t-butyldimethylsilyl, pivaloyl and the like, or esters such as acetate, propionate, benzoate and the like, or $P^1$ and $P^2$ together represent methylene dioxy, isopropylidene, benzylidene, 1-phenyl ethylidene, carbonate and the like.

The present invention also provides a process for the preparation of the compound of formula (X), their stereoisomers, their polymorphs, their pharmaceutically acceptable salts and their pharmaceutically acceptable solvates, which comprises:

(i) protecting the hydroxy groups present on carbons 3 or 19 or 3 and 19 together in the compound of formula (VII)

with suitable protecting groups using conventional methods to produce a compound of formula (VIII),

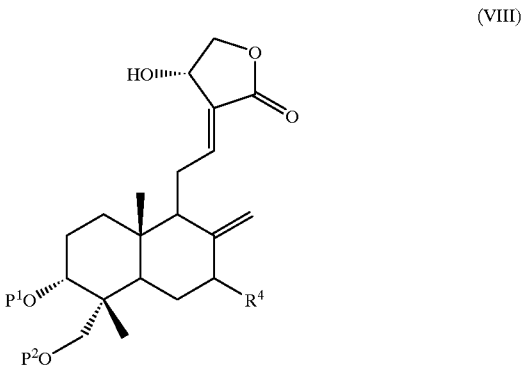

(VIII)

where $R^4$ represents hydrogen; $P^1$ and $P^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene, carbonate and the like, (ii) reacting the compound of formula (VIII) defined above with compound of formula (IX)

$R^1$—L (IX)

where $R^1$ and L have the meanings given above to produce a compound of formula (X),

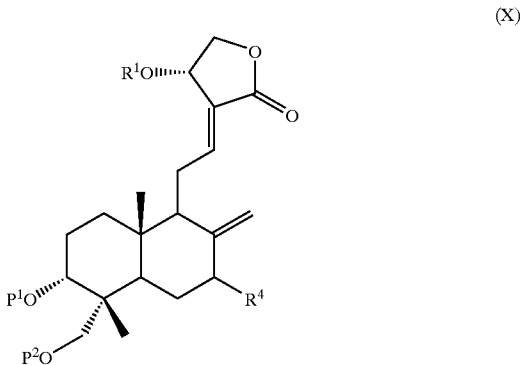

(X)

where $R^1$, $R^4$, $P^1$ and $P^2$ are as defined earlier.

The protection of a compound of formula (VII) may be carried out using trityl chloride, t-butyldimethylsilyl chloride, pivaloyl chloride, dimethylsulfoxide, acetone, 2,2-dimethoxy propane, trimethyl ortho acetate, benzaldehyde, p-methoxy benzaldehyde and the like. The reaction may be carried out in the presence of a suitable catalyst such as $SOCl_2$, $H_2SO_4$, $HClO_4$, pyridinium p-toluene sulphonate, pyridine, p-toluene sulfonic acid, dimethyl aminopyridine, and the like. The reaction may be carried out in the absence or presence of suitable solvent such as benzene, DMF, DMSO, acetonitrile, DCM, and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h. The reaction of a compound of formula (VIII) with a compound of formula (IX) to produce a compound of formula (X) may be carried out in the presence of dicyclohexylcarbodiimide (DCC), diethyl azadicarboxylate (DEAD), diisopropyl azadicarboxylate (DIAD) and the like. The reaction may be carried out in the absence or presence of a base selected from triethylamine, pyridine, dimethyl aminopyridine and the like. The reaction may be carried out in the presence of solvents such as dichloromethane, chloroform, $C_6H_6$, dimethyl sulfoxide, methanol, ethanol and the like or mixtures thereof. The reaction may be carried out at a temperature in the range of 0° C. to 200° C., preferably at a temperature in the range of 20° C. to 160° C. and the reaction time may range from 2 to 12 h, preferably from 2 to 10 h.

In yet another embodiment of the present invention there is provided a novel intermediate of formula (XI)

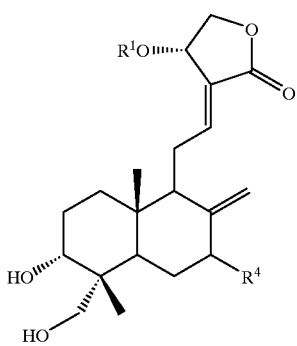

(XI)

where $R^1$ represents hydrogen or substituted or unsubstituted groups selected from alkyl, aryl, heteroaryl, aralkyl, heteroaralkyl, alkanoyl, alkenoyl, aroyl, aralkanoyl, aralkenoyl, heteroaroyl, heteroaralkanoyl, heteroaralkenoyl, sulfonyl groups or a group —(CO)—W—$R^5$ where W represents O, S or $NR^6$, wherein $R^6$ represents hydrogen or substituted or unsubstituted $(C_1-C_6)$alkyl group, $R^5$ represents substituted or unsubstituted groups selected from alkyl, aryl, aralkyl or aroyl and $R^4$ represents hydrogen.

The present invention also provides a process for the preparation of the compound of formula (XI), their stereoisomers, their polymorphs, their pharmaceutically acceptable salts and their pharmaceutically acceptable solvates, which comprises:

(i) protecting the hydroxy groups present on carbons 3 or 19 or 3 and 19 together in the compound of formula (VII) with suitable protecting groups using conventional methods to produce a compound of formula (VIII),

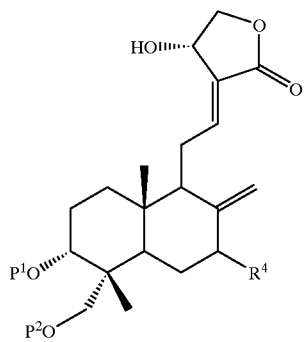

(VIII)

where $R^4$ represents hydrogen; $P^1$ and $P^2$ may be same or different and represent hydrogen, trityl, t-butyl dimethyl silyl, pivaloyl and the like or esters such as acetate, propionate, benzoate and the like or together may form methylene dioxy, isopropylidene, benzylidene, 1-phenyl ethylidene, carbonate and the like, (ii) reacting the compound of formula (VIII) defined above with compound of formula (IX)

$R^1$—L     (IX)

where $R^1$ and L have the meanings given above to produce a compound of formula (X),

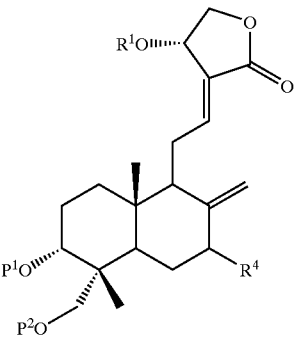

(X)

where $R^1$, $R^4$, $P^1$ and $P^2$ are as defined earlier, (iii) deprotecting the compound of formula (X) by conventional methods to produce a compound of formula (XI),

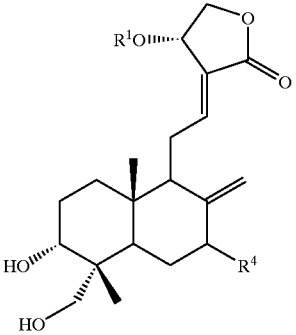

(XI)

where $R^1$ and $R^4$ have the meanings given above.

The protection of a compound of formula (VII) may be carried out using trityl chloride, t-butyldimethylsilyl chloride, pivaloyl chloride, dimethylsulfoxide, acetone, 2,2-dimethoxy propane, trimethyl ortho acetate, benzaldehyde, p-methoxy benzaldehyde and the like. The reaction may be carried out in the presence of a suitable catalyst such as $SOCl_2$, $H_2SO_4$, $HClO_4$, pyridinium p-toluene sulphonate, pyridine, p-toluene sulfonic acid, dimethyl aminopyridine, and the like. The reaction may be carried out in the absence or presence of suitable solvent such as benzene, DMF, DMSO, acetonitrile, DCM, and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h. The reaction of a compound of formula (VIII) with a compound of formula (IX) to produce a compound of formula (X) may be carried out in the presence of dicyclohexylcarbodiimide (DCC), diethyl azadicarboxylate (DEAD), diisopropyl azadicarboxylate (DIAD) and the like. The reaction may be carried out in the absence or presence of a base selected from triethylamine, pyridine, dimethyl aminopyridine and the like. The reaction may be carried out in the presence of solvents such as dichloromethane, chloroform, $C_6H_6$, dimethyl sulfoxide, methanol, ethanol and the like or mixtures thereof. The reaction may be carried out at a temperature in the range of 0° C. to 200° C., preferably at a temperature in the range of 20° C. to 160° C. and the reaction time may range from 2 to 12 h, preferably from 2 to 10 h.

The deprotection of a compound of formula (X) to produce a compound of formula (XI) may be carried out using deprotecting agent such as acetic acid, hydrochloric acid, formic acid, trifluoroacetic acid and the like. The reaction may be carried in the presence of suitable solvent such as water, THF, dioxane, DCM, $CHCl_3$, methanol and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h.

It is appreciated that in any of the above-mentioned reactions, any reactive group in the substrate molecule may be protected according to conventional chemical practice. Suitable protecting groups in any of the above-mentioned reactions are those used conventionally in the art. The methods of formation and removal of such protecting groups are those conventional methods appropriate to the molecule being protected.

The compound of formula (I) when produced through an intermediate compound, conventional functional group transformations such as hydrolysis, reduction or oxidation may be carried out.

For example, the compound of formula (I) where $R^1$, $R^2$ or $R^3$ are multi substituted and the two substituents may form a linking group —X—$(CR^{11}R^{12})_n$—Y—, which may be converted to a compound of formula (I), where $R^1$, $R^2$ or $R^3$ are multisubstituted and the substituents are independent.

The pharmaceutically acceptable salts are prepared by reacting the compounds of formula (I), formula (X) or formula (XI) wherever applicable with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, tromethamine, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds of formula (I), formula (X) and formula (XI) forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like or chiral bases such as brucine, cinchona alkaloids and their derivatives and the like. Commonly used methods are compiled by Jaques et al. in "Enantiomers, Recemates and Resolution" (Wiley Interscience, 1981).

Various polymorphs of compound of general formula (I), formula (X) and formula (XI) forming part of this invention may be prepared by crystallization of compound of formula (I), formula (X) or formula (XI) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or slow cooling. The presence of polymorphs may be determined by solid probe nmr spectroscopy, ir spectroscopy, differential scanning calorimetry, powder X-ray data or such other techniques.

Pharmaceutically acceptable solvates of compounds of formula (I), formula (X) and formula (XI) forming part of this invention may be prepared by conventional methods such as dissolving the compounds of formula (I) in solvents such as water, methanol, ethanol etc., preferably water and recrystallizing by using different crystallization techniques.

The present invention also envisages pharmaceutical compositions containing compounds of the formula (I), formula (X), formula (XI), or their stereoisomers, their polymorphs, their pharmaceutically acceptable salts, their pharmaceutically acceptable solvates or their mixtures in combination with the usual pharmaceutically employed carriers, solvents, diluents and other media normally employed in preparing such compositions.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 25%, preferably 1 to 15% by weight of active compound, the remainder of the composition may be pharmaceutically acceptable carriers, diluents or solvents and also contain other active ingredients.

The compounds of the formulae (I), (X) and (XI) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. The injectable solutions prepared in this manner can then be administered intravenously, intraperitoneally, subcutaneously, or intramuscularly, with intramuscular administration being preferred in humans. The invention is explained in detail in the examples given below which are provided by way of illustration only and therefore should not be construed to limit the scope of the invention.

EXAMPLE 1

Preparation of 3,19-isopropylidene andrographolide

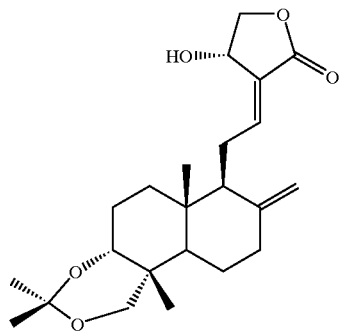

A mixture of andrographolide (15 g), 2,2-dimethoxy propane (20 ml) and a catalytic amount of pyridinium p-toluene sulphonate in benzene/dimethyl sulphoxide (300 ml/40 ml) was refluxed for 30 min. After completion of the reaction (checked by TLC), the contents were cooled to room temperature and treated with excess triethylamine (10 ml) to quench the remaining catalyst. The reaction mixture was diluted with benzene (200 ml) and washed with water (3×300 ml). The organic layer was separated, dried over $Na_2SO_4$ and concentrated to obtain a yellow coloured solid which on maceration with diethyl ether gave 3,19-isopropylidene andrographolide as a pale yellow product (16.5 g). m.p. 194.5° C., m/z 390.

$^1$H NMR (CDCl$_3$): δ 7.0(t, 1H, H-12), 5.1(d, 1H, H-14), 4.95(s, 1H, H-17a), 4.65(s, 1H, H-17b), 4.5(m), 4.3(d, 1H), 4.0(d, 1H, H-19a), 3.5(dd, 1H, H-3), 3.2(d,1H, H-19b), 2.6(m), 1.45(s, 3H), 1.35(s, 3H), 1.2(s, 3H), 1.0 (s, 3H).

| Example No. | Structure | Mol. formula/ Mol. wt & melting point | Spectral data |
|---|---|---|---|
| 2 | 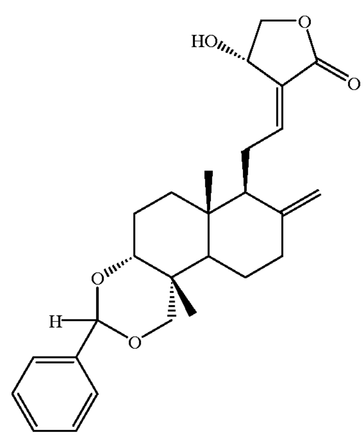 | $C_{27}H_{34}O_5$ m/z: 438 m.p.: 142–143° C. | $^1$H NMR (CDCl$_3$): δ 7.6–7.3(m), 7.0(t, 1H, H-12), 5.8(s, 1H), 5.0(d, 1H, H-14), 4.85(s, 1H, H-17a), 4.6(s, 1H, H-17b), 4.4(m), 4.3(m), 3.7–3.5(m), 2.7–2.2(m), 1.5(s, 3H), 0.9(s, 3H). |
| 3 | 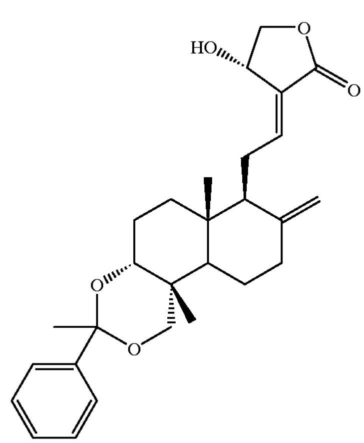 | $C_{28}H_{36}O_5$ M/z: 452 m.p.: 201–203° C. | $^1$H NMR (CDCl$_3$): δ 7.6–7.2(m), 6.95(t, 1H, H-12), 5.0(d, 1H, H-14), 4.85(s, 1H, H-17a), 4.50(s, 1H, H-17b), 4.4(m), 4.2(dd, 1H), 4.1(d, 1H, H-19a), 3.6(dd, 1H, H-3), 3.3(d, 1H, H-19b), 2.4(m), 1.5(s, 3H), 1.4(s, 3H), 0.4(s, 3H). |

EXAMPLE 4

Preparation of 3,19-isopropylidene-14-(N-Boc-methionyl)andrographolide

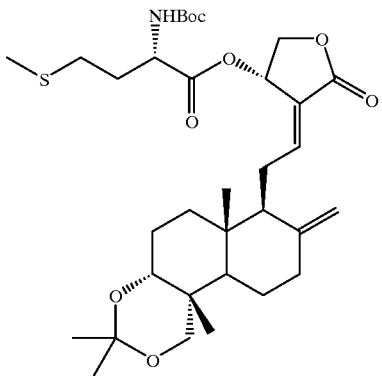

Mixed anhydride of N-Boc methionine and ethyl chloroformate was prepared by adding ethyl chloroformate (0.548 ml, 0.64 mmol) to a mixture of N-Boc methionine (1.5 g, 0.64 mmol) and triethyl amine (0.643 ml) in dichloromethane (20 ml) at −40° C. and the contents were stirred for 5 min.

To the above mixed anhydride, a mixture of 3,19-isopropylidene andrographolide (500 mg; 0.128 mmol) (obtained in Example 1) and triethylamine (0.64 ml) in dichloromethane (20 ml) was added at −40° C. The reaction mixture was brought to room temperature and stirred for 4 hours. The reaction was monitored by TLC. After completion of the reaction, the reaction mixture was diluted with dichloromethane, washed with aq. NaHCO₃ and water successively. The organic layer was separated, dried over Na₂SO₄ and concentrated. The residue was chromatographed over a column of silica gel (230–400 mesh; with chlorfororm:acetone as eluting system) to obtain 3,19-isopropylidene 14-(N-Boc-methionyl)andrographolide (250 mg) as a colourless solid. m.p:70° C., m/z: 621.

¹H NMR (CDCl₃): δ 7.1(t, 1H, H-12), 6.0(d, 1H, H-14), 5.05(d), 4.95(s, 1H, H-17a), 4.6(m), 4.4(m), 4.3(m), 4.0(d, 1H, H-19a), 3.5(m, 1H, H-3), 3.2(d, 1H, H-19b), 2.5(m), 2.2(s), 2.15(s), 2.1-1.7(m), 1.5(m), 1.3(m), 0.95(s).

The compounds of Example 5 & 6 are prepared by a procedure similar to those of Examples 1–4.

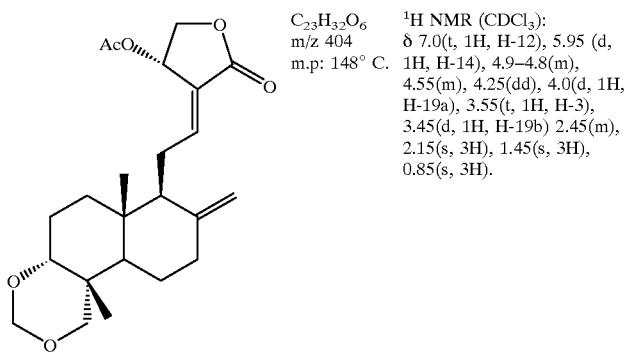

5 | C₂₃H₃₂O₆ m/z 404 m.p: 148° C. | ¹H NMR (CDCl₃): δ 7.0(t, 1H, H-12), 5.95 (d, 1H, H-14), 4.9–4.8(m), 4.55(m), 4.25(dd), 4.0(d, 1H, H-19a), 3.55(t, 1H, H-3), 3.45(d, 1H, H-19b) 2.45(m), 2.15(s, 3H), 1.45(s, 3H), 0.85(s, 3H).

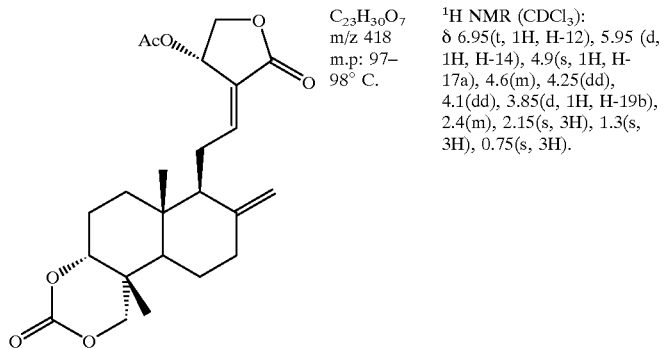

6 | C₂₃H₃₀O₇ m/z 418 m.p: 97–98° C. | ¹H NMR (CDCl₃): δ 6.95(t, 1H, H-12), 5.95 (d, 1H, H-14), 4.9(s, 1H, H-17a), 4.6(m), 4.25(dd), 4.1(dd), 3.85(d, 1H, H-19b), 2.4(m), 2.15(s, 3H), 1.3(s, 3H), 0.75(s, 3H).

EXAMPLE 7

Preparation of 14-acetyl andrographolide

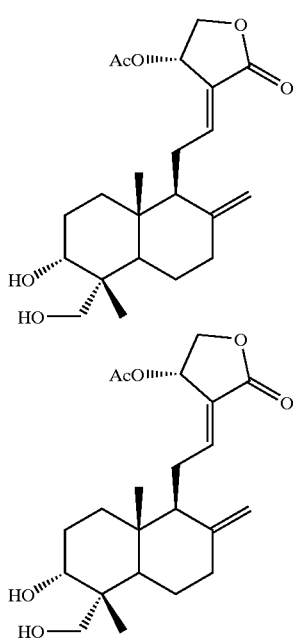

Step 1

A mixture of 3,19-isopropylidene andrographolide (15 g), obtained in Example 1, and distilled acetic anhydride (110 ml) were refluxed for 45 min. The reaction was monitored by TLC. After completion of the reaction, the contents were cooled to room temperature, diluted with water (500 ml) and extracted with dichloromethane (3×200 ml). The organic layer was separated, dried over $Na_2SO_4$ and concentrated to obtain a brown oily material. The crude material was purified by flash column chromatography (silica gel 230–400 mesh; 250 g; eluting system light petrol:ethyl acetate=85:15) to obtain pure 3,19-isopropylidene-14-acetyl andrographolide (13 g).

Step 2

3,19-Isopropylidene-14-acetyl andrographolide (13 g) obtained in step 1 was treated with 75 ml of aq. acetic acid (acetic acid:water=7:3) and the contents were stirred for 10 min at room temperature till a clear solution was obtained. The contents were diluted with dichloromethane (500 ml), washed with water (3×300 ml) followed by aq. sodium bicarbonate (2×300 ml). The organic layer was separated, dried over $Na_2SO_4$ and concentrated to get crude 14-acetyl andrographolide as a pale yellow coloured solid which was purified by crystallising in ethyl acetate and light petrol (11.2 g). m.p. 169° C., m/z 392.

$^1$H NMR ($CDCl_3$): δ 7.0(t, 1H, H-12), 5.9(d, 1H, H-14), 4.90(s, 1H, H-17a), 4.60(m), 4.2(dd), 3.9(d, 1H, H-19a), 3.5(t, 1H, H-3), 3.4(d, 1H, H-19b), 2.1(s, 3H), 1.2(s, 3H), 0.8(s, 3H).

EXAMPLE 8

Preparation of 14-chloroacetyl andrographolide

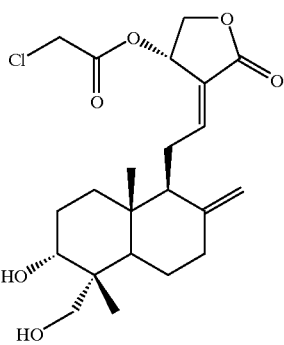

Step 1

To a mixture of 3,19-isopropylidene andrographolide (1 g) (obtained in Example 1), triethyl amine (1.26 ml) in dichloromethane (50 ml), chloro acetyl chloride (0.84 ml) was added. The contents were stirred for 15 min. The reaction was monitored by TLC. After confirming the completion of the reaction, the reaction mixture was diluted with dichloromethane, washed with water, dried over $Na_2SO_4$ and concentrated to furnish 14-chloroacetyl-3,19-isopropylidene andrographolide.

Step 2

14-Chloracetyl-3,19-isopropylidene andrographolide (300 mg) obtained in step 1 was treated with 30 ml of aq. acetic acid (acetic acid:water=7:3) at room temperature for 10 min. The reaction was monitored by TLC. After completion of the reaction, the reaction mixture was diluted with water, neutralized with solid $NaHCO_3$, extracted with dichloromethane. The organic layer was concentrated and the residue was chromatographed over a column of silica gel (230–400 mesh; using chlorform:acetone=95:5 as an eluent) to get 14-chloroacetyl andrographolide (500 mg). M.p. 144.5° C., m/z 426.

$^1$H NMR ($CDCl_3$): δ 7.1(t, 1H, H-12), 6.0(d, 1H, H-14), 4.9(s, 1H, H-17a), 4.6(dd, 2H, H-15), 4.5(s, 1H, H-17b), 4.3(d), 4.2(d, 1H, H-19a), 4.1(s, 2H), 3.5(t, 1H, H-3), 3.35(d, 1H, H-19b), 2.45(m), 1.8(m), 1.3(s, 3H), 0.7(s, 3H).

EXAMPLE 9

Preparation of 14-phenylcarbamoyl andrographolide

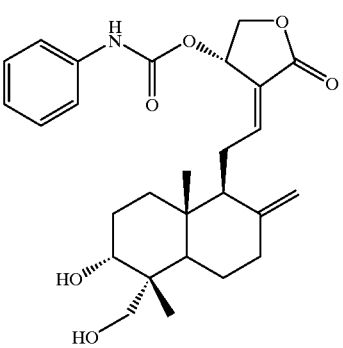

Step 1

To a mixture of 3,19-isopropylidene andrographolide (500 mg) (obtained in Example (1), triethylamine (0.4 ml) in dichloromethane (40 ml), phenyl isocyanate (0.2 ml) was added. The contents were stirred for 1 h. The reaction was monitored by TLC. After completion of the reaction, the reaction mixture was diluted with dichloromethane, washed with water and dried over $Na_2SO_4$ and concentrated to give 14-carbamoyl-3,19-isopropylidene andrographolide.

Step 2

14-Carbamoyl-3,19-isopropylidene andrographolide obtained in step 1 was treated with 30 ml of aq. acetic acid (acetic acid:water=7:3) for 10 min at room temperature. The reaction was monitored by TLC. After completion of the reaction, the reaction mixture was diluted with water, neutralized with solid $NaHCO_3$ and extracted with dichloromethane. The residue obtained after removal of the solvent was chromatographed over a column of silica gel (230–400 mesh; using chloroform: acetone 97:3 as an eluent) to obtain 14-carbamoyl andrographolide (600 mg). m.p. 120° C., m/z 469.

$^1$H NMR ($CDCl_3$): δ 7.4(m), 7.1(m), 6.7(s), 6.0(d, 1H, H-14), 4.9(s, 1H, H-17a), 4.55(m), 4.4(d), 4.15(d, 1H, H-19a), 3.5(t, 1H, H-3), 3.3(d, 1H, H-19b), 2.5(m), 1.85(m), 1.25(s, 3H), 0.65(s, 3H).

EXAMPLE 10

Preparation of 14-(N-isopropyl)carbamoyl andrographolide

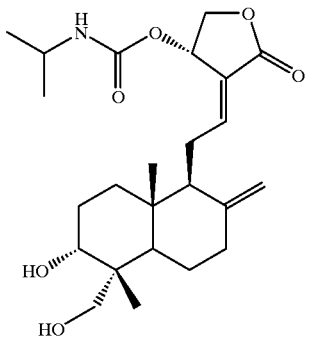

Step 1

N-Isopropyl isocyanate was prepared by adding a solution of isopropyl amine (1.2 ml) and triethyl amine (1.87 ml) in toluene (10 ml) to a stirred solution of triphosgene (1.25 g) in 30 ml toluene and heated at 100° C. for 1 h. The reaction mixture was cooled, to this a solution of 3,19-isopropylidene andrographolide (700 mg)(obtained in example 1) and triethyl amine (1.87 ml) in toluene (25 ml) was added. The contents were stirred for 48 h at room temperature. The reaction was monitored by TLC. After completion of the reaction, the reaction mixture was diluted with dichloromethane, washed with water and dried over $Na_2SO_4$. Concentration of the organic layer yielded 3,19-isopropylidene-14-(N-isopropyl)carbamoyl andrographolide.

Step 2

3,19-Isopropylidene-14-(N-isopropyl)carbamoyl andrographolide obtained in step 1 was treated with 20 ml of aq acetic acid (acetic acid:water=7:3) for 20 min at room temperature. The reaction was monitored by TLC. After completion of the reaction, the reaction mixture was diluted with water, neutralized with solid $NaHCO_3$ and extracted with dichloromethane. The residue obtained after removal of the solvent was chromatographed over a column of silicagel (230–400 mesh; using chlorform: acetone 97:3 as an eluent) to obtain 14-(N-isopropyl)carbamoyl andrographolide (250 mg) as a colourless solid. m.p. 122° C., m/z 435.

$^1$H NMR (DMSO): δ 8.3(s), 6.8(t, 1H, H-12), 5.9(d, 1H, H-14), 4.8(s, 1H, H-17a), 4.6(m), 4.5(s, 1H, H-17b), 4.2(d), 3.8(d), 3.6(t), 3.45(s), 3.3(m), 2.2-2.6(m), 1.9(m), 1.7(m), 1.05 (m), 0.65(s, 3H).

The compounds of Example 11–15 are prepared by a procedure similar to those of Examples 7–10.

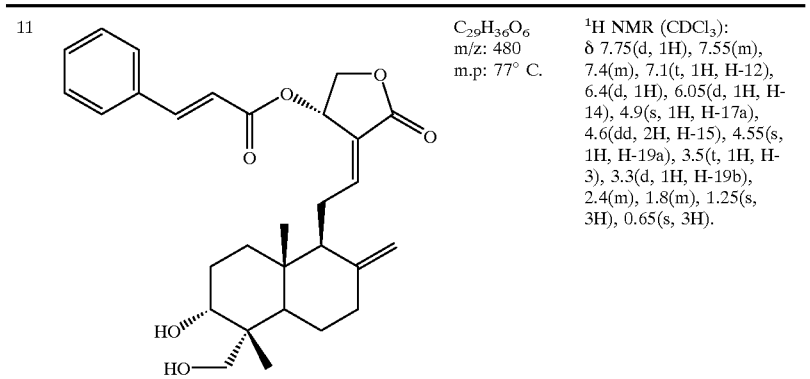

| 11 | | $C_{29}H_{36}O_6$<br>m/z: 480<br>m.p: 77° C. | $^1$H NMR ($CDCl_3$):<br>δ 7.75(d, 1H), 7.55(m), 7.4(m), 7.1(t, 1H, H-12), 6.4(d, 1H), 6.05(d, 1H, H-14), 4.9(s, 1H, H-17a), 4.6(dd, 2H, H-15), 4.55(s, 1H, H-19a), 3.5(t, 1H, H-3), 3.3(d, 1H, H-19b), 2.4(m), 1.8(m), 1.25(s, 3H), 0.65(s, 3H). |

-continued

| 12 | 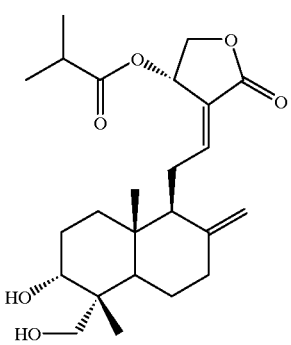 | C$_{24}$H$_{36}$O$_6$<br>m/z: 420<br>m.p.: 122.6° C. | $^1$H NMR (CDCl$_3$):<br>δ 7.0(t, 1H, H-12), 5.95 (d, 1H, H-14), 4.9(s, 1H, H-17a), 4.55(dd, 2H, H-15), 4.5(s, 1H, H-17b), 4.2(d, 1H, H-19a), 3.5(t, 1H, H-3), 3.35 (d, 1H, H-19b), 2.6(m), 2.4(m), 1.8(m), 1.2(m, 9H), 0.65(s, 3H). |
| --- | --- | --- | --- |
| 13 | 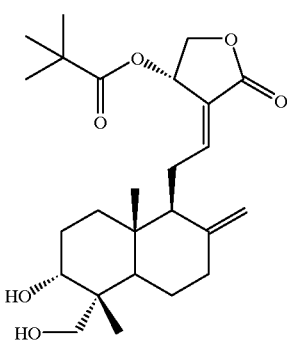 | C$_{25}$H$_{38}$O$_6$<br>m/z: 434<br>m.p.: 172.7° C. | $^1$H NMR (CDCl$_3$):<br>δ 7.0(t, 1H, H-12), 5.85(d, 1H, H-14), 4.85(s, 1H, H-17a), 4.59(dd, 2H, H-15), 4.45(s, 1H, H-17b), 4.1(m), 3.45(t, 1H, H-3), 3.3(d, 1H, H-19b), 2.4(m), 1.8(m), 1.25(s), 1.2(s), 0.6(s, 3H). |
| 14 | 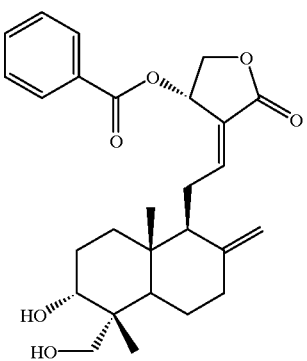 | C$_{27}$H$_{34}$O$_6$<br>m/z: 454<br>m.p: 85.5–87° C. | $^1$H NMR (CDCl$_3$):<br>δ 8.05(d), 7.65(t), 7.5(t), 7.1(t,1H, H-12) 6.18(d, 1H, H-14), 4.85(s, 1H, H-17a), 4.7(dd, 2H, H-15), 4.55(s, 1H, H-17b), 4.4(d), 4.15(d, 1H, H-19a), 3.45(t, 1H, H-3), 3.3(d, 1H, H-19b), 2.5(m), 2.0–1.4(m) 1.25(s, 3H), 0.6 (s, 3H). |
| 15 | 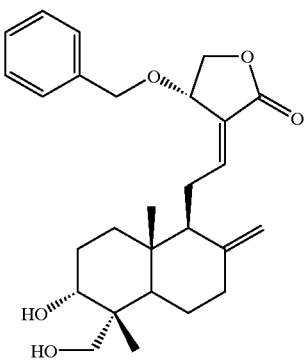 | C$_{27}$H$_{36}$O$_5$<br>m/z: 430<br>m.p.: 141° C. | $^1$H NMR (CDCl$_3$):<br>δ 7.39(s, 5H), 7.0(t, 1H, H-12), 4.9(s, 1H, H-17a), 4.8(d, 1H, H-14), 4.6(s), 4.5(d), 4.39(m), 4.2(d, 1H, H-19a), 3.4(dd, 1H, H-3), 3.35(d, 1H, H-19b), 2.4(m), 1.4–2.0(m), 1.25(s, 3H), 0.65 (s, 3H). |

EXAMPLE 16

3,19-Diacetyl-14-(2'-acetyl 3'-acetamido 3'-phenyl) propionyl andrographolide

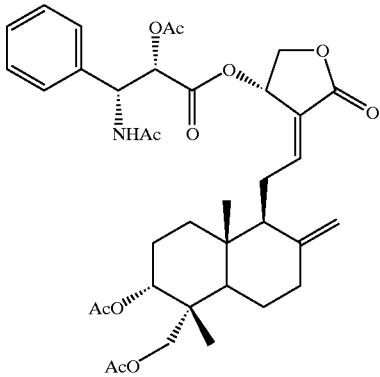

Step 1

To a mixture of 3,19-isopropylidene andrographolide (8.0 g, 20.51 mmol) (obtained in Example 1), [4S,5R-(N-t-butoxycarbonyl)-2,2-dimethyl-4-phenyl-5-oxazolidine carboxylic acid] (16.44 g, 51.21 mmol) and dicyclohexyl carbodimide (10.56 g, 51.2 mmol) in dichloromethane (300 ml), triethyl amine (14.27 ml, 102.56 mmol) were added at room temperature. The contents were stirred for 1 h. The reaction was monitored by TLC. After confirming the completion of the reaction, the precipitated dicyclohexyl urea was filtered. The organic layer was washed with saturated aq. $NaHCO_3$ and water successively, dried over $Na_2SO_4$ and concentrated. The residue was chromatographed over a column of silica gel (230–400 mesh; with chloroform:acetone=98:2 as an eluent) to obtain 14-[4'S, 5'R-(N-t-butoxycarbonyl)-2',2'-dimethyl-4'-phenyl-5'-oxazolidine]carbonyl 3,19-isopropylidene andrographolide (9 g, 63.3%) as a colourless solid.

$^1$H NMR ($CDCl_3$): δ 7.3(m), 7.1(t, 1H, H-12), 6.05(d, 1H, H-14), 5.0(m), 4.9(s, 1H, H-17a), 4.5(m), 4.25(d), 3.95(d, 1H, 19a), 3.5(dd, 1H, H-3), 3.2(d, 1H, H-19b), 2.4(m), 1.8(s, 3H), 1.7(s, 3H), 1.4(s, 3H), 1.3(s, 3H), 1.15(s, 3H), 0.9(s, 3H).

Step 2

To a solution of 14-[4'S,5'R-(N-t-butoxycarbonyl)-2',2'-dimethyl-4'-phenyl-5'-oxazolidine]carbonyl 3,19-isopropylidene andrographolide obtained in step 1, in acetic anhydride (50 ml) at 80° C., zinc chloride (500 mg) was added in 100 mg portions over a period of 30 min. Stirring continued for another 30 min. The reaction was monitored by TLC. After confirming the completion of the reaction, the reaction mixture was poured into water, extracted with dichloromethane, dried over $Na_2SO_4$ and concentrated. The residue was chromatographed over a column of silica gel (230–400 mesh; with light petrol:acetone=8:2 as an eluent) to obtain 3,19-Diacetyl-14-(2'-acetyl 3'-acetamido 3'-phenyl)propionyl andrographolide (5 g, 56.5%) as a colourless solid. m.p. 105° C., m/z 681.

1H NMR ($CDCl_3$): δ 7.3(m), 7.05(t, 1H, H-12), 6.15(d, 1H), 5.8(d, 1H, H-14), 5.65(d, 1H), 5.2(s, 1H), 4.9(s, 1H, H-17a), 4.65(s, 1H, H-17b), 4.55(m), 4.35(d, 1H), 4.25(d, 1H), 4.1(d, 1H), 2.6(m), 2.4(m), 2.1(s), 2.0(s), 1.9–1.3(m), 1.0(s, 3H), 0.75(s, 3H).

EXAMPLE 17

3,19-Diacetyl-14-[4'S,5'R-(N-t-butoxycarbonyl)-2',2'-dimethyl-4'-phenyl-5'-oxazolidine]carbonyl andrographolide

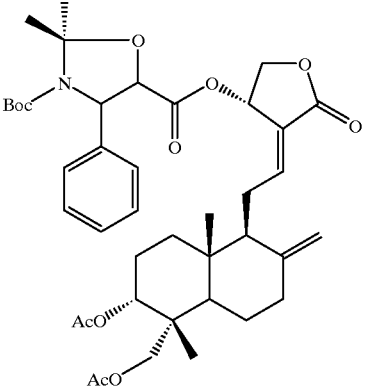

Step 1

3,19-diacetyl-14-(2'-acetyl 3'-acetamido 3'-phenyl) propionyl andrographolide (1.75 g, 2.53 mmol) obtained in step 1 of the Example 16, was treated with 100 ml of aq. acetic acid (acetic acid:water=7:3) at room temperature for 10 min till a clear solution was obtained. The reaction was monitored by TLC. After confirming the completion of the reaction, the reaction mixture was poured into water, extracted with dichloromethane. The organic layer was separated, dried over $Na_2SO_4$ and concentrated to obtain 14-[4'S,5'R-(N-t-butoxycarbonyl)-2',2'-dimethyl-4'-phenyl-5'-oxazolidine] carbonyl andrographolide (1.65 g), which was used further without purification.

Step 2

14-[4'S,5'R-(N-t-butoxycarbonyl)-2',2'-dimethyl-4'-phenyl-5-oxazolidine]carbonyl andrographolide (1.15 g) obtained above was refluxed in acetic andhydride (40 ml) for about 15 min. The reaction was monitored by TLC. After confirming the completion of the reaction, the reaction mixture was cooled, poured into water, extracted with dichloromethane, the organic layer separated, dried over $Na_2SO_4$ and concentrated. The residue was chromatographed over a column of silica gel (230–400 with light petrol:acetone=9:1 as an eluent) to get 3,19-Diacetyl-14-[4'S,5'R-(N-t-butoxycarbonyl]-2',2'-dimethyl-4'-phenyl-5'-oxazolidine] carbonyl andrographolide (1.2 g, 92.45%). m.p. 88.4° C., m/z 737.

$^1$H NMR ($CDCl_3$): δ 7.3(m), 7.05(t, 1H, H-12), 6.05(d, 1H, H-14), 5.0(m), 4.9(s, 1H, H-17a), 4.6(m), 4.49(m), 4.3(dd), 4.1(d), 2.4(m), 2.15(s, 3H), 2.05(s, 3H), 1.8(s, 3H), 1.7(s, 3H), 1.55(s, 9H), 1.05(s, 3H), 0.7(s, 3H).

EXAMPLE 18

Preparation of 3,19-Diacetyl-14-(2'hydroxy-3'-benzoylamino 3'-phenyl)propionyl andrographolide

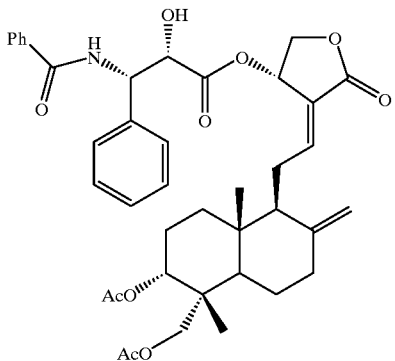

3,19-Diacetyl-14-[4'S,5'R-(N-t-butoxycarbonyl)-2',2'-dimethyl-4'-phenyl-5'-oxazolidine]carbonyl andrographolide (compound obtained in Example 17) (500 mg) was treated with 15 ml of trifluoroacetic acid and dichloromethane mixture (1:1) at room temperature for 20 min. The reaction mixture was neutralized with saturated aq. NaHCO$_3$ and to this was added benzoylchloride (0.2 ml) in ethyl acetate (15 ml). The contents were stirred for 30 min. The reaction was monitored by TLC. After confirming the completion of the reaction, the reaction mixture was extracted with ethyl acetate, the organic layer was separated, dried over Na$_2$SO$_4$ and concentrated. The residue was chromatographed over a column of silica gel (230–400 mesh; using chloroform:acetone mixture=94:6 as an eluent) to obtain 3,19-Diacetyl-14-(2'hydroxy-3'-benzoylamino 3'-phenyl)propionyl andrographolide (200 mg) as a colourless solid. m.p. 202.6° C., m/z 701.

$^1$H NMR (CDCl$_3$): δ 8.0(d), 7.9(d), 7.55(s), 7.3–7.5(m), 7.05(t, 1H, H-12), 5.9(d, 1H, H-14), 5.7(d), 4.9(s, 1H, H-17a), 4.65(s, 1H, H-17b), 4.6(m), 4.3(d), 4.0(d), 2.05(s, 6H), 1.9–1.2(m), 1.05 (s, 3H), 0.65(s, 3H).

EXAMPLE 19

Preparation of 3,19-Diacetyl-14-(2'hydroxy-3-N-Boc amino 3'-phenyl)propionyl andrographolide

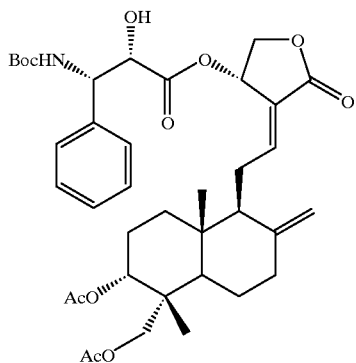

3,19-Diacetyl-14-[4'S,5'R-(N-t-butoxycarbonyl)-2',2'-dimethyl-4'-phenyl-5'-oxazolidine]carbonyl andrographolide (compound obtained in example 17) (400 mg) was treated with a 15 ml of trifluoroacetic acid and dichloromethane mixture (1:1) at room temperature for 20 min. The reaction mixture was neutralized with saturated aq. NaHCO$_3$ and to this was added a mixture of di-tertiary butyl dicarbonate (307 mg) and ethyl acetate (15 ml). The contents were stirred for 30 min. The reaction was monitored by TLC. After confirming the completion of the reaction, the reaction mixture was extracted with ethyl acetate; the organic layer was separated, dried over Na$_2$SO$_4$ and concentrated. The residue was chromatographed over a column of silica gel (230–400 mesh; with light petrol:acetone=9:1 as an eluent) to obtain 3,19-Diacetyl-14-(2'hydroxy-3-N-Boc amino 3'-phenyl) propionyl andrographolide (200 mg) as a colourless solid. m.p. 101.8° C., m/z 697.

$^1$H NMR (CDCl$_3$): δ 7.4(m), 7.1(t, 1H, H-12), 5.9(d, 1H, H-14), 5.4(dd), 5.1(s, 1H), 5.0(s, 1H, H-17a), 4.65(s, 1H, H-17b), 4.6(m), 4.35(t), 4.1(d), 2.1(s, 6H), 1.45(s), 1.05(s, 3H), 0.8(s, 3H).

EXAMPLE 20

Preparation of 14-(N-Boc-glycinyl)-3,19-dipropionyl andrographolide

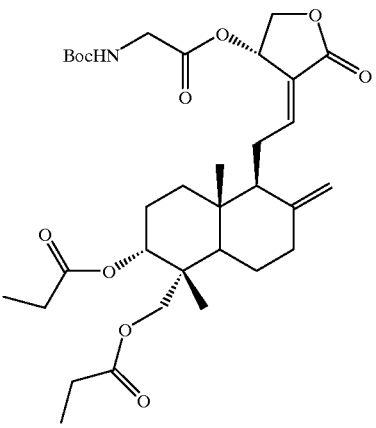

Step 1

Mixed anhydride of N-Boc-glycine and ethyl chloroformate was prepared by adding ethyl chloroformate (0.5 ml) to a mixture of N-Boc-glycine (1 g) and triethylamine (0.5 ml) in dichloromethane (20 ml) at −40° C. and the contents were stirred for 15 mm.

To the above mixed anhydride, a mixture of 3,19-isopropylidene andrographolide (500 mg) (obtained in Example 1) and triethylamine (0.5 ml) in dichloromethane (10 ml) was added at −40° C. The reaction mixture was brought to room temperature and stirred for 13 h. The reaction was monitored by TLC. After completion of the reaction, the reaction mixture was diluted with dichloromethane, washed with aq. NaHCO$_3$ and water successively. The organic layer was separated, dried over Na$_2$SO$_4$ and concentrated. The residue was chromatographed over a column of silica gel (230–400 mesh; eluting system chloroform:acetone=98:2) to obtain 3,19-isopropylidene-14-(N-Boc-glycinyl) andrographolide (300 mg).

Step 2

3,19-Isopropylidene-14-(N-Boc-glycinyl) andrographolide (300 mg) obtained in step 1 was treated with 20 ml of aq. Acetic acid (acetic acid:water=7:3) at room temperature for 10 min till a clear solution was obtained. The reaction was monitored by TLC. After completion of the reaction, the reaction mixture was diluted with water, neutralized with solid NaHCO₃, and extracted with dichloromethane. The organic layer was concentrated and the residue was chromatographed over a column of silica gel (230–400 mesh; using chloroform:acetone=90:10 as an eluent) to get 14-(N-Boc-glycinyl)andrographolide (200 mg).

Step 3

14-(N-Boc-glycinyl)andrographolide (200 mg) (obtained in step 2) was refluxed in propionic anhydride (20 ml) for about 10 min. The reaction was monitored by TLC. After confirming the completion of the reaction, the reaction mixture was cooled, poured into water, extracted with dichloromethane. The organic layer was separated, dried over Na₂SO₄ and concentrated. The residue was chromatographed over a column of silica gel (230–400 mesh; using chloroform:acetone=97:3 as an eluent) to obtain 14-(N-Boc-glycinyl)-3,19-dipropionyl andrographolide (150 mg) as a colourless solid. m.p. 65° C., m/z 619.

¹H NMR (CDCl₃): δ 7.05(t, 1H, H-12), 6.0(d, 1H, H-14), 4.95(m), 4.9(s, 1H, H-17a), 4.7–4.5(m), 4.3(m), 4.2(d, 1H, H-19a), 3.95(d), 2.5–2.25(m), 2.0–1.7(m), 1.5(s), 1.15(m), 1.05(s, 3H), 0.75(s, 3H).

EXAMPLE 21

Preparation of 14-(N-Boc-glycinyl -3,19-diacetyl andrographolide

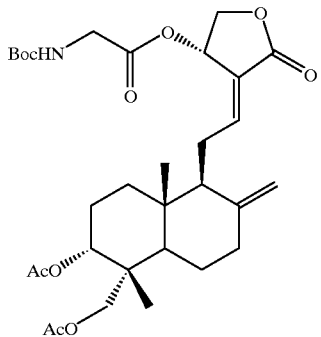

14-(N-Boc-glycinyl)andrographolide (300 mg) (obtained in Example 20, step 2) was refluxed in acetic anhydride (15 ml) for about 15 min. The reaction was monitored by TLC. After confirming the completion of the reaction, the reaction mixture was cooled, poured into water, extracted with dichloromethane. The organic layer was separated, dried over Na₂SO₄ and concentrated. The residue was chromatographed over a column of silica gel (230–400 mesh; using chloroform:acetone=98:2 as an eluent) to obtain 14-(N-Boc-glycinyl)-3,19-diacetyl andrographolide (260 mg) as a colourless solid. m.p. 67° C., m/z 591.

¹H NMR (CDCl₃): δ 7.05(t, 1H, H-12), 6.0(d, 1H, H-14), 4.9(s, 1H, H-17a), 4.6(m), 4.5(s, 1H, H-17b), 4.4(m), 4.1(d), 3.9(d), 2.45(m), 2.05(s, 6H), 2.0–1.1(m), 1.05(s, 3H), 0.75(s, 3H).

EXAMPLE 22

Preparation of 14-(N-acetyl-glycinyl)-3,19-diacetyl andrographolide

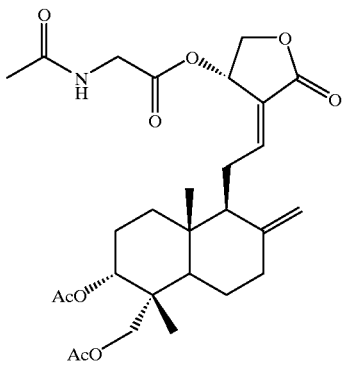

A mixture of 14-(N-Boc-glycinyl)andrographolide (300 mg) (obtained in Example 20, step 2) in acetic anhydride (10 ml) with a catalytic amount of zinc chloride was heated at 80° C. for about 5 min. The reaction was monitored by TLC. After confirming the completion of the reaction, the reaction mixture was cooled, poured into water and extracted with dichloromethane. The organic layer was separated, dried over Na₂SO₄ and concentrated. The residue was chromatographed over a column of silica gel (230–400 mesh; using chloroform:acetone=98:2 as an eluent) to obtain 14-(N-acetyl-glycinyl)-3,19-diacetyl andrographolide (200 mg) as a colourless soild. m.p. 196° C., m/z 533.

¹H NMR (CDCl₃): δ 7.05(t, 1H, H-12), 6.0(m), 4.9(s, 1H, H-17a), 4.6(m), 4.5(s, 1H, H-17b), 4.3(m), 4.15(d), 4.05(d), 2.4(m), 2.05(s), 1.05(s, 3H), 0.75(s, 3H).

EXAMPLE 23

Preparation of 14-(N-benzoyl glycinyl)-3,19-diacetyl andrographolide

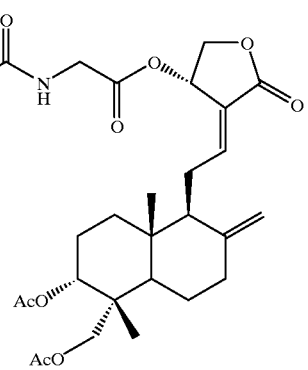

14-(N-Boc-glycinyl)-3,19-diacetyl andrographolide (390 mg) (obtained by the procedure used in Example 21) was treated with a 20 ml of trifluoroacetic acid and dichloromethane mixture (1:1) at room temperature for 10 min. The reaction mixture was neutralized with saturated aq. NaHCO₃ and to this was added benzoylchloride (0.35 ml) in ethyl acetate (50 ml). The contents were stirred at room temperature for 40 min. The reaction was monitored by TLC. After confirming the completion of the reaction, the reaction mixture was extracted with ethyl acetate; the organic layer was separated, dried over $Na_2SO_4$ and concentrated. The residue was chromatographed over a column of silica gel (230–400 mesh; using chloroform:acetone=96:4 as an eluent) to obtain 14-(N-benzoylglycinoyl)- -3,19-diacetyl andrographolide(200 mg) as a colourless solid. m.p. 104° C., m/z 595.

$^1$H NMR ($CDCl_3$): δ 7.8(d), 7.5(m), 7.05(t, 1H, H-12), 6.65(t), 6.0(d, 1H, H-14), 4.9(s, 1H, H-17a), 4.6(m), 4.3(m), 4.1(d, 1H), 2.4(m), 2.05(s, 6H), 1.1–2.0(m), 1.05(s, 3H), 0.75(s, 3H).

EXAMPLE 24

Preparation of 3,19-diacetyl-14-O-ethyl andrographolide

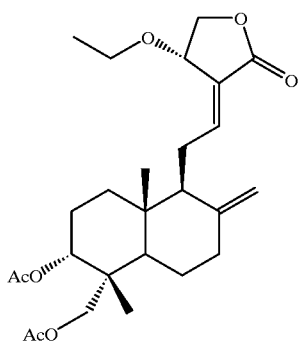

Step 1

A mixture of 3,19-isopropylidene andrographolide (500 mg), obtained in example 1, calcium sulphate (555 mg), silver oxide (500 mg) and ethyl iodide (5 ml) were stirred at room temperature for 18 h. The reaction was monitored by TLC. After confirming the completion of the reaction, the inorganic solids were filtered, washed with dichloromethane. The organic washings were concentrated and the residue obtained was chromatographed over a column of silica gel (230–400 mesh; using chloroform:acetone mixture=98:2 as an eluent) to obtain 14-O-ethyl-3,19-isopropylidene andrographolide (300 mg) as a colourless solid.

Step 2

14-O-Ethyl-3,19-isopropylidene andrographolide (300 mg) obtained in step 1, was treated with 50 ml of aq. acetic acid (acetic acid:water=7:3) at room temperature for about 10 min. The reaction was monitored by TLC. After confirming the completion of the reaction, the reaction mixture was diluted with water, neutralized with solid $NaHCO_3$ and extracted with dichloromethane. The organic layer on concentration gave 14-O-ethyl andrographolide (250 mg, 92%) as a colourless solid.

Step 3

14-O-Ethyl andrographolide (250 mg) obtained in step 2, was refluxed in acetic anhydride (10 ml) for about 10 min. The reaction was monitored by TLC. After confirming the completion of the reaction, the reaction mixture was cooled, diluted with water, extracted with dichloromethane and the organic layer was concentrated. The residue was chromatographed over a column of silica gel (230–400 mesh; using light petrol:acetone mixture=8:2 as an eluent) to obtain 3,19-diacetyl-14-O-ethyl andrographolide (170 mg, 55.7%). m.p. 125.7° C., m/z 462.

$^1$H NMR ($CDCl_3$): δ 7.0(t, 1H, H-12), 4.9(s, 1H,H-17a), 4.75(m), 4.7(s, 1H, H-17b), 4.6(m), 4.39(m), 4.15(d), 3.55 (m), 2.5(m), 2.05(s, 6H), 2.0–1.3(m), 1.25(t), 1.05(s, 3H), 0.8 (s, 3H).

EXAMPLE 25

Preparation of 3,19-diacetyl-14-O-methyl andrographolide

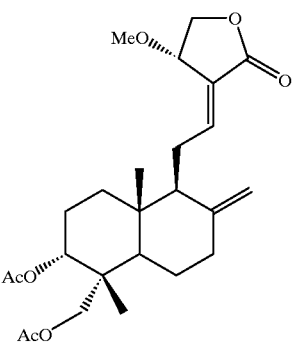

Step 1

A mixture of 3,19-isopropylidene andrographolide (500 mg) (obtained in Example 1), calcium sulphate (500 mg), silver oxide (480 mg) and methyl iodide (1.5 ml) were stirred at room temperature for 18 h. The reaction was monitored by TLC. After confirming the completion of the reaction, the reaction mixture was diluted with dichloromethane, inorganic solids were filtered, washed with dichloromethane. The organic filtrate and the washings were concentrated and the residue obtained was chromatographed over a column of silica gel (230–400 mesh; using chloroform:acetone mixture=99:1 as an eluent) to obtain 14-O-methyl-3,19-isopropylidene andrographolide (550 mg).

Step 2

14-O-methyl-3,19-isopropylidene andrographolide (550 mg) obtained in step 1, was treated with 25 ml of methanolic HCl (25 ml methanol:200 μl HCl) at room temperature for about 2–5 min. The reaction was monitored by TLC. After confirming the completion of the reaction, the reaction mixture was diluted with water, neutralized with solid $NaHCO_3$ and extracted with dichloromethane. The organic layer on concentration gave 14-O-methyl andrographolide (250 mg) as a colourless solid.

Step 3

14-O-methyl andrographolide (250 mg) obtained in step 2, was refluxed in acetic anhydride (10 ml) for about 10 min. The reaction was monitored by TLC. After confirming the completion of the reaction, the reaction mixture was cooled, diluted with water, extracted with dichloromethane and the organic layer was concentrated. The residue was chromatographed over a column of silica gel (230–400 mesh; using chloroform:acetone mixture=95:5 as an eluent) to obtain 3,19-diacetyl-14-O-methyl andrographolide (150 mg). m.p. 129–130° C., m/z 448.

$^1$H NMR ($CDCl_3$): δ 7.05(t, 1H, H-12), 4.9(s, 1H, H-17a), 4.75(m), 4.7(s, 1H, H-17b), 4.6(m), 4.39(m), 4.15(d), 3.35(s, 3H), 2.5(m), 2.05(s, 6H), 2.0–1.2(m), 1.05(s, 3H), 0.8 (s, 3H).

EXAMPLE 26

Preparation of 3,19-diacetyl-14-(3,4-dimethoxy) cinnamoyl andrographolide

Step 1

Mixed anhydride of 3,4-dimethoxy cinnamic acid and ethyl chloroformate was prepared by dropwise addition of ethyl chloroformate (1.25 ml) to a stirred solution of 3,4-dimethoxy cinnamic acid (2.4 g) and triethyl amine (1.5 ml) in dichloromethane (100 ml) at 0° C. under $N_2$ atmosphere. The contents were stirred for another 30 min at the same temperature.

A mixture of 3,19-isopropylidene andrographolide (1.5 g) (compound obtained in Example 1), triethyl amine (1.5 ml) in dichloromethane (25 ml) was added to the above solution at 0° C. After the addition, the reaction mixture was brought to room temperature and the contents were stirred for 12 h. The reaction was monitored by TLC. After completion of the reaction, the reaction mixture was diluted with dichloromethane, washed with saturated aq. $NaHCO_3$, followed by water and dried over $Na_2SO_4$. The organic layer was concentrated and the residue was chromatographed over a column of silica gel (230–400 mesh; using chloroform:acetone=98:2 as an eluent) to obtain 14-(3,4-dimethoxy)cinnamoyl-3,19-isopropylidene andrographolide (700 mg).

Step 2

14-(3,4-Dimethoxy)cinnamoyl-3,19-isopropylidene andrographolide obtained in step 1 (700 mg) was treated with 100 ml of aq. acetic acid (acetic acid:water=7:3) for 10 min at room temperature. The reaction was monitored by TLC. After completion of the reaction, the reaction mixture was diluted with water, neutralized with solid $NaHCO_3$ and extracted with dichloromethane. Concentration of the organic extract gave 14-(3,4-dimethoxy)cinnamoyl andrographolide (650 mg).

A mixture of 14-(3,4-dimethoxy)cinnamoyl andrographolide (650 mg) and acetic anhydride (10 ml) was refluxed for about 15 min. The reaction was monitored by TLC. After completion of the reaction, the reaction mixture was cooled, diluted with water and extracted with dichloromethane. The organic layer was concentrated and the residue was chromatographed over a column of silica gel (230–400 mesh; using light petrol:acetone=85:15 as an eluent) to obtain 3,19-diacetyl-14-(3,4-dimethoxy) cinnamoyl andrographolide (230 mg) as a colourless solid. m.p. 121.6° C., m/z 624.

$^1$H NMR ($CDCl_3$): δ 7.7(d, 1H), 7.1(m), 6.9(d), 6.3(d), 6.1(d, 1H, H-14), 4.9(s, 1H, H-17a), 4.6(m), 4.35(m), 4.1(d), 3.9(s, 6H), 2.5(m), 2.05(s, 6H), 1.8(m), 1.3(m), 1.0(s, 3H), 0.7(s, 3H).

EXAMPLE 27

Preparation of 14-(3,4-dimethoxy)cinnamoyl-3,19-dipropionyl andrographolide

A mixture of 14-(3,4-dimethoxy)cinnamoyl andrographolide (350 mg) (obtained in Example 26) and propionic anhydride(5 ml) was refluxed for about 15 min. The reaction was monitored by TLC. After completion of the reaction, the reaction mixture was cooled, diluted with water and extracted with dichloromethane. The organic layer was concentrated and the residue was chromatographed over a column of silica gel (230–400 mesh; using light petrol:acetone=85:15 as an eluent) to obtain 14-(3,4-dimethoxy)cinnamoyl-3,19-dipropionyl andrographolide (210 mg) as a colourless solid. m.p 85.4° C., m/z: 652.

$^1$H NMR (CDC13): δ 7.7(d, 1H), 7.1(m), 6.9(d), 6.3(d), 6.1(d, 1H, H-14), 4.9(s, 1H, H-17a), 4.6(dd, 2H, H-15), 4.55(s, 1H, H-17b), 4.3(d), 4.15(d), 3.9(s, 6H), 2.5(m), 2.3(m), 1.8(m), 1.3(m), 1.1(m), 1.0(s,3H), 0.7(s, 3H).

EXAMPLE 28

Preparation of 3-acetyl andrographolide

Step 1

A mixture of andrographolide (5 g) and trityl chloride (10 g) in dry pyridine (30 ml) was heated at 60° C. for 6 h. The reaction was monitored by TLC. After completion of the reaction, the reaction mixture was cooled, diluted with diethylether. The organic layer was washed with aq copper sulphate solution followed by water and dried over Na$_2$SO$_4$. The residue obtained after removal of the solvent was chromatographed over a column of silica gel (230–400 mesh; using light petrol:ethyl acetate=6:4 as an eluent) to obtain 19-trityl andrographolide (5.0 g).

Step 2

19-Trityl andrographolide (1.0 g) obtained in the above step, was refluxed in distilled acetic anhydride (40 ml) for 5 min. After completion of the reaction (monitored by TLC), the contents were cooled to room temperature, diluted with water and extracted with dichloromethane. The organic layer was separated, dried over Na$_2$SO$_4$ and concentrated. The crude material was purified by flash column chromatography (silica gel: 230–400 mesh; eluting system chloroform and acetone 95:5) to obtain pure 3–acetyl–19-trityl andrographolide (300 mg).

Step 3

3-Acetyl-19-trityl andrographolide (300 mg) obtained in step 2 was treated with a mixture of formic acid and dichloromethane (1:1) (10 ml) for 10 min at room temperature. The reaction was monitored by TLC. After completion of the reaction, the reaction mixture was diluted with ethyl acetate, washed with aq. NaHCO$_3$ followed by water and dried over Na$_2$SO$_4$. The residue obtained after removal of the solvent was chromatographed over a column of silicagel (230–400 mesh; using chloroform: acetone 92:8 as an eluent) to obtain 3-acetyl andrographolide (100 mg) as a colourless solid. m.p. 205° C., m/z 392.

$^1$H NMR (CDCl$_3$): δ 6.95(t, 1H, H-12), 5.0(d, 1H, H-14), 4.9(s, 1H, H-17a), 4.65(m), 4.6(s, 1H, H-17b), 4.45(dd, 1H, H-3), 4.25(d), 4.15(d, 1H, H-19a), 3.4(d, 1H, H-19b), 2.5 (m), 2.1(s, 3H), 1.2–2.0(m), 1.1(s, 3H), 0.7(s, 3H).

EXAMPLE 29

Preparation of 3,14-diacetyl andrographolide

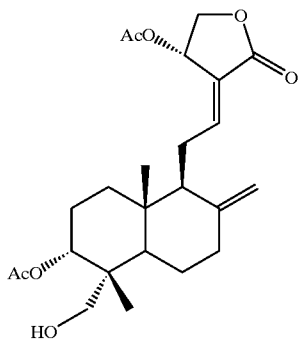

Step 1

19-Trityl andrographolide (1.0 g) was refluxed in distilled acetic anhydride (40 ml) for 30 min. After completion of the reaction (monitored by TLC), the contents were cooled to room temperature, diluted with water and extracted with dichloromethane. The organic layer was separated, dried over Na$_2$SO$_4$ and concentrated. The crude material was purified by flash column chromatography (silica gel: 230–400 mesh; eluting system chloroform:acetone=95:5) to obtain pure 3,14-diacetyl-19-trityl andrographolide (800 mg).

Step 2

3,14-Diacetyl-19-trityl andrographolide (800 mg) obtained in step 1 was treated with a mixture of formic acid and dichloromethane (1:1) 20 ml for 10 min at room temperature. The reaction was monitored by TLC. After completion of the reaction, the reaction mixture was diluted with ethyl acetate, washed with aq. NaHCO$_3$ followed by water and dried over Na$_2$SO$_4$. The residue obtained after removal of solvent was chromatographed over a column of silica gel (230–400 mesh; using chlorform:acetone=95:5 as an eluent) to obtain 3,14-diacetyl andrographolide (500 mg) as a colourless solid. m.p. 100° C. m/z 434.

$^1$H NMR (CDCl$_3$): δ 7.0(t, 1H, H-12), 5.9(d, 1H, H-14), 4.9(s, 1H, H-17a), 4.65(dd), 4.55–4.5(m), 4.25(d), 4.15(d, 1H, H-19a), 3.4(d, 1H, H-19b), 2.4(m), 2.15(s, 3H), 2.1(s, 3H), 2.0–1.2(m), 1.1(s, 3H), 0.7(s, 3H).

EXAMPLE 30

Preparation of 3,14,19,7-tetraacetyl andrographolide

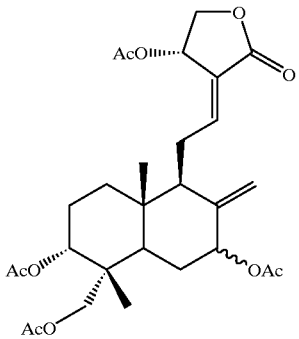

Step 1

To a suspension of selenium dioxide (200 mg) in dichloromethane (25 ml), tert-butyl hydroperoxide (0.28 μl) was added and the mixture was stirred for 10 min. 3,14,19-triacetyl andrographolide (1 g) in dichloromethane (5 ml) was added to the above mixture and the contents were stirred overnight.

The reaction was monitored by TLC. After completion of the reaction, the reaction mixture was diluted with dichloromethane, washed with water and dried over Na$_2$SO$_4$. The residue obtained after removal of solvent was chromatographed over a column of silica gel (230–400 mesh; using chloroform: acetone as an eluent) to obtain 7-hydroxy-3,14,19-triacetyl andrographolide (410 mg).

Step 2

7-hydroxy-3,14,19-triacetyl andrographolide (150 mg) was refluxed in acetic anhydride (10 ml) for about 15 min. The reaction was monitored by TLC. After confirming the completion of the reaction, the reaction mixture was cooled, poured into water and extracted with dichloromethane. The organic layer was separated, dried over Na$_2$SO$_4$ and concentrated. The residue was chromatographed over a column of silica gel (230–400 mesh; using chloroform: acetone as an eluent) to obtain 3,14,19,7-tetraacetyl andragrapholide (100 mg) as a colourless solid. m.p. 70° C., m/z 534.

$^1$HNMR(CDCl$_3$): δ 6.9(t, 1H, H-12), 5.95(d, 1H, H-14), 5.4(s), 5.25(s, 1H, H-17a), 4.75(s, 1H, H-17b), 4.6(m), 4.4–4.1(m), 2.2–2.0(m, 12H), 0.95(s, 3H), 0.75(s, 3H).

Anti-cancer Activity

The compounds prepared in the present invention exhibited good in vitro anti-cancer activity towards various human tumor cell lines.

Each test compound was screened against a battery of cell lines representing eight different types of cancers. In a typical procedure, 1×10$^4$ cells were seeded into each well of 96 well plate in 100 μL volume of RPMI 1640 medium containing antibiotics and 10% FCS.

The plates were incubated at 37° C. in presence of CO$_2$. After 24 h, test compounds were evaluated at five 10 fold dilutions ranging from 100 to 0.01 μM. To each test well 100 μL of test compound solution was added and medium with vehicle was added to control wells and the plates were further incubated. After 48 h of incubation, plates were terminated by Sulforhodamine B method.

The optical density which is proportional to protein mass, is then read by automated spectrophotometric plate reader at a wavelength of 515 nm. Readings were transferred to a microcomputer and mean 50% Growth Inhibition (GI50). The compounds of the present invention showed anticancer activity, which can be seen from the data given below:

| PANEL/CELL LINE | GROWTH INHIBITION (GI 50) [μM] Example Nos. | | | | | | | |
|---|---|---|---|---|---|---|---|---|
| | 1 | 3 | 9 | 14 | 15 | 16 | 18 | 22 |
| BREAST: | | | | | | | | |
| MCF-7/ADR | 2.0 | 2.0 | 0.4 | 3.5 | 20.0 | 5.5 | 8.0 | 8.0 |
| MCF7 | 13.0 | 12.0 | 2.5 | 10.0 | 6.0 | 5.0 | | |
| CNS: | | | | | | | | |
| U251 | 4.0 | 2.0 | 6.5 | 1.5 | 40.0 | 4.0 | 8.0 | 1.5 |
| COLON: | | | | | | | | |
| SW-620 | 5.0 | 5.0 | 2.5 | 3.0 | 3.5 | 6.0 | 5.0 | 5.0 |
| HT29 | 2.0 | 2.0 | 4.0 | 4.0 | 3.5 | 6.5 | | |
| LUNG: | | | | | | | | |
| H522 | 14.0 | 12.0 | 12.0 | 7.5 | 12.0 | 6.0 | 20.0 | 20.0 |
| MELANOMA: | | | | | | | | |
| UACC62 | 4.0 | 3.0 | 3.0 | 3.0 | 3.5 | 3.0 | | |
| M14 | | | | | | | 3.0 | 9.5 |
| OVARIAN: | | | | | | | | |
| SKOV-3 | 8.0 | 5.0 | 3.0 | 3.5 | 3.0 | 4.0 | 4.0 | 30.0 |
| OVCAR | | | | | | — | | |
| PA1 | 2.0 | 19.0 | | | | 2.0 | | |
| PROSTATE: | | | | | | | | |
| DU145 | | | 6.0 | 6.0 | 4.0 | 6.5 | 3.0 | 8.0 |
| PC-3 | | | 3.0 | 2.0 | 2.0 | 6.5 | | |
| RENAL: | | | | | | | | |
| A498 | 13.0 | 3.0 | | | | 9.0 | 10.0 | 25.0 |
| ACHN | | | 5.0 | 5.0 | 4.0 | — | | |

Anti HIV Activity

Human CD$^4$+ T cell line PM-1 used in the assay was cultured in RPMI-1640 medium containing 10% Fetal bovine serum, 2 g/L sodium bicarbonate, 100,000 units/L Pencillin-G and 100 mg/L streptomycin. Healthy PM-1 cells were plated on the first day in a 96 well plate at 2×10$^6$ cells per well. After 24 h HIV-1/MN was added to the culture and incubated for 2 h for infection. Cells were washed twice with PBS to remove the virus in the culture. Different concentrations of DRF compounds ranging from 10$^{-4}$ to 10$^{-8}$ M were added to the culture and incubated for 96 h. The viability of cells was then assessed by standard MTT assay and the viral antigen P24 levels were estimated by ELISA method. Based on the MTT assay values the P 24 antigen values were corrected.

All the samples were tested in triplicates and the average was used for calculations. AZT was used as standard compound for comparision.

| Example | Concentration | Percentage Inhibition |
|---|---|---|
| 16 | 1 μM | 61.06 |
| AZT | 1 μM | 72.47 |

Lymphocyte Proliferation

Human lymphocytes were isolated from whole blood by using Ficoll Hypaque Plus (Amersham). On day one, 1 million lymphocytes were seeded into each well of 96 well plate in 100 μL volume of RPMI 1640 medium containing 10% FCS and Phytohemagglutitin A at 1 μg/well concentration. Plates were incubated at 37° C. in CO$_2$ incubator for 24 h. Test compounds at various concentrations were added to test wells and only medium with vehicle was added to control wells. After 48 h of incubation 0.5 mCi of tritiated thymidine was added to each well. After 24 h of thymidine addition the cells were harvested and the incorporated radioactivity was determined.

Stimulation Index (SI) was calculated using the formula, $$SI = \frac{A^T - A^C}{A^C} \times 100$$

| Example No. | Concentration | Stimulation Index (SI) |
|---|---|---|
| 16 | 1 μM | 90 |

$A^T$ = Average CPM of treated wells,
$A^C$ = Average CPM of control wells.

Metabolic Disorders (a) Efficacy in Generic Models:

Mutution in colonies of laboratory animals and different sensitivities to dietary regimens have made the development of animal models with non–insulin dependent diabetes and hyperlipidemia associated with obesity and insulin resistance possible. Genetic models such as db/db mice have been developed by the various laboratories for understanding the pathophysiology of disease and testing the efficacy of new antidiabetic compounds (Diabetes, (1983) 32: 830–838; Annu. Rep. Sankyo Res. Lab. (1994) 46:1–57). The homozygous animals, C57 BL/KsJ–db/db mice developed by Jackson Laboratory, US, are obese, hyperglycemic, hyperinsulinemic and insulin resistant (J. Clin, Invest., (1990) 85: 962–967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

Male C57BL/KsJ-db/db mice of 8 to 14 week age, having body weight range of 35 to 60 grams, bred at Dr. Reddy's Research Foundation (DRF) animal house, were used in the experiment. The mice were provided with standard feed (National Institute of Nutrition (NIN), Hyderabad, India) and acidified water, ad libitum. The animals having more than 350 mg/dl blood sugar were used for testing. The number of animals in each group was 4.

Test compounds were suspended in chremophore/DMSO/ $H_2O$ and administered to test group at a dose of 1 mg to 500 mg/kg through oral gavage daily for 6 days. The control group received vehicle (dose 10 ml/1 g). On $6^{th}$ day the blood samples were collected one hour after administration of test compounds/vehicle for assessing the biological activity.

The random blood sugar and triglyceride levels were measured by collecting blood (100 $\mu$l) through orbital sinus, using heparinised capillary in tubes containing EDTA which was centrifuged to obtain plasma. The plasma glucose and triglyceride levels were measured spectrometrically, by glucose oxidase and glycerol-3-$PO_4$ oxidase/peroxidase enzyme (Dr. Reddy's Lab. Diagnostic Division Kits, Hyderabad, India) methods respectively.

The blood sugar and triglycerides lowering activities of the test compound was calculated according to the formula:

$$\text{Percent reduction}(\%) = \left[1 - \frac{TT/OT}{TC/OC}\right] \times 100$$

OC = Zero day control group value
OT = Zero day treated group value
TC = Test day control group value
TT = Test day treated group value Body weight of the animals were measured at the beginning and at the end of the study period.

No adverse effects were observed for any of the mentioned compounds of invention in the above test.

The experimental results from the db/db mice, suggest that the novel compounds of the present invention also possess therapeutic utility as a prophylactic or regular treatment for diabetes, obesity, cardiovascular disorders such as hypertension, hyperlipidaemia and other diseases; as it is known from the literature that such diseases are interrelated to each other.

|  |  | Percentage reduction | |
| --- | --- | --- | --- |
| Example | Dose (mg/kg) | TG | Glucose |
| 16 | 100 | 54 | 64 |

(b) Plasma Triglyceride and Body Weight Reduction in Swiss Albino Mice

Male Swiss albino mice (SAM) were obtained from NIN and housed in DRF animal house. All these animals were maintained under 12 hour light and dark cycle at 25±1° C. Animals were given standard laboratory chow (NIN, Hyderabad, India) and water, ad libitum. SAM of 20–25 g body weight range (Oliver, P., Plancke, M. O., Marzin, D., Clavey, V., Sauzieres, J and Fruchart, J. C. Effects of fenofibrate, gemfibrozil and nicotinic acid on plasma lipoprotein levels in normal and hyperlipidemic mice. Atherosclerosis. 1988. 70: 107–114)

The test compounds were administered orally to Swiss albino mice at 30 to 500 mg/kg/day dose for 6 days. Control mice were treated with vehicle (Chremophore/DMSO/$H_2O$; dose 10 ml/kg).

The blood samples were collected in fed state 1 hour after drug administration on 0 and 6 day of treatment. The blood was collected from the retro-orbital sinus through heparinised capillary in EDTA containing tubes. After centrifugation, plasma sample was separated for triglyceride (Wieland, 0. Methods of Enzymatic analysis, Bergerneyer, H. O., Ed., 1963. 211–214; Trinder, P. Ann. Clin. Biochem. 1969. 6: 24–27). Measurement of plasma triglycerides was done using commercial kits (Dr. Reddy's Diagnostic Division, Hyderabad, India).

|  |  | Percentage reduction | |
| --- | --- | --- | --- |
| Example | Dose (mg/kg) | TG | Body weight |
| 16 | 100 | 42 | 9 |
|  | 250 | — | 15 |
|  | 500 | 62 | 23 |

The formula used to measure percent reduction in blood sugar/triglycerides is given above.

What is claimed is:

1. A compound of the formula (I),

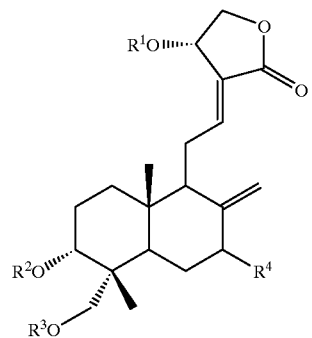

(I)

where $R^1$, $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, aralkanoyl, aralkenoyl, heteroaralkanoyl, heteroaralkenoyl, sulfonyl group or a group —(CO)—W—$R^5$ where W represents O, S or $NR^6$, wherein $R^6$ represents hydrogen or substituted or unsubstituted ($C_1$–$C_6$)alkyl group, $R^5$ represents substituted or unsubstituted groups selected from alkyl, aryl, aralkyl or aroyl or $OR^2$ and $OR^3$ together form a substituted or unsubstituted 6 or 7 membered cyclic structure containing carbon and oxygen atoms; $R^4$ represents hydrogen, halogen or $XR^7$ where X represents O, S, or NH and $R^7$ represents hydrogen or substituted or unsubstituted groups selected from alkyl, aryl, aralkyl, alkenoyl, alkanoyl, aroyl, heteroaroyl, aralkenoyl, aralkanoyl, sulfonyl groups or a group —(CO)—NH—$R^8$ where $R^8$ represents substituted or unsubstituted groups selected from alkyl, aryl, aralkyl; with provisos that (i) $R^1$, $R^2$ and $R^3$ may be same except when they represent hydrogen or alkanoyl group and (ii) when $R^2$ and $R^3$ represent hydrogen, $R^1$ does not represent unsubstituted alkanoyl; its stereoisomers, its polymorphs, its salts and its solvates.

2. The compound according to claim 1, where the cyclic structures formed by $OR^2$ and $OR^3$ are selected from —O—$(CR^9R^{10})_m$—O— wherein $R^9$ and $R^{10}$ are the same or different and independently represent hydrogen, or unsubstituted or substituted groups selected from $(C_1–C_6)$ alkyl; aryl group, heteroaryl group or $R^9$ and $R^{10}$ together represent C=O; and m represents an integer 1 or 2.

3. The compound according to claim 1, wherein the substituents on $R^1$, $R^2$, $R^3$, $R^7$ and $R^8$ are selected from cyano, hydroxy, nitro, thio, halogen, or substituted or unsubstituted group selected from $(C_1–C_8)$ alkyl, amino, mono or disubstituted amino group; alkanoyl, thio$(C_1–C_8)$alkyl; $(C_1–C_6)$alkoxy, aroyl, acyloxy, substituted or unsubstituted aryl, heteroaryl, acylamino, aralkylamino, alkoxycarbonylamino, aryloxycarbonylamino, aralkoxycarbonylamino groups, $(C_1–C_8)$alkylthio, heteroarylthio, acylthio, aralkylthio, arylthio, $(C_1–C_8)$alkylseleno, acylseleno, aralkylseleno, arylseleno or COOR where R represents hydrogen or $(C_1–C_6)$alkyl groups.

4. The compound according to claim 1, wherein the substituents on $R^5$ are selected from halogen atom; amino group, cyano, hydroxy, nitro, trifluoroethyl, $(C_1–C_6)$ alkyl, or $(C_1–C_6)$ alkoxy.

5. The compound according to claim 1, wherein the substituents on $R^6$ are selected from halogen atom, amino group, cyano, hydroxy, nitro, trifluoroethyl, $(C_1–C_6)$ alkyl, or $(C_1–C_6)$ alkoxy.

6. The compound according to claim 1, wherein when the aryl group is disubstituted, the two substituents on the adjacent carbon atoms form a linking group —X—$CH_2$—Y—, or —X—$CH_2$—$CH_2$—Y—, where X and Y are same or different and independently represent O, NH, S or $CH_2$.

7. The compound according to claim 1, wherein when the groups represented by $R^1$, $R^2$, $R^3$, $R^5$, $R^7$ and $R^8$ are multisubstituted, the substituents present on the adjacent carbons form a linking group —X—$(CR^{11}R^{12})_n$—Y— where $R^{11}$ and $R^{12}$ represent $(C_1–C_8)$ alkyl, X and Y are same or different and independently represent $CH_2$, O, S or NH; and n is 1 or 2.

8. A compound selected from:

3,19-Isopropylidene andrographolide;

3,19-Benzylidene andrographolide;

3,19-(1-Phenylethylidene)andrographolide;

3,19-Isopropylidene-14-(N-Boc methionyl) andrographolide;

14-Acetyl 3,19-methylenedioxy andrographolide;

14-Acetyl 3,19—O—cyclic carbonyl andrographolide;

14-Acetyl andrographolide;

14-Chloroacetyl andrographolide;

14-(Phenylcarbamoyl)andrographolide;

14-(N-Isopropyl carbamoyl)andrographolide;

14-Cinnamoyl andrographolide;

14-Isopropanoyl andrographolide;

14-Pivaloyl andrographolide;

14-Benzoyl andrographolide;

14-Benzyl andrographolide;

3,19-Diacetyl-14-(2'-acetyl-3'-acetamido 3'-phenyl) propionyl andrographolide;

3,19-Diacetyl-14-[4'S,5 'R-(N-t-Butoxycarbonyl)-2',2'-dimethyl-4'-phenyl-5'-oxazolidine]carbonyl andrographolide;

3,19-Diacetyl-14-(2'hydroxy-3'-benzoylamino 3'-phenyl) propionyl andrographolide;

3,19-Diacetyl-14-(2'hydroxy-3-N-Boc amino-3'-phenyl) propionyl andrographolide;

14-(N-Boc-glycinyl)-3,19-dipropionyl andrographolide;

14-(N-Boc-glycinyl)-3,19-diacetyl andrographolide;

14-(N-Acetylglycinyl)-3,19-diacetyl andrographolide;

14-(N-Benzoylglycinyl)-3,19-diacetyl andrographolide;

3,19-Diacetyl-14—O—ethyl andrographolide;

3,19-Diacetyl-14—O—methyl andrographolide;

3,19-Diacetyl-14-(3,4-dimethoxycinnamoyl) andrographolide;

14-(3,4-dimethoxy)cinnamoyl-3,19-dipropionyl-andrographolide;

3-Acetyl andrographolide;

3,14-Diacetyl andrographolide;

3,14,19,7-Tetra acetyl andrographolide;

3,19-Isopropylidene-14-acetyl andrographolide;

14-Chloroacetyl-3,19-isopropylidene andrographolide;

14-Carbamoyl-3,19-isopropylidene andrographolide;

3,19-Isopropylidene-14-(N-isopropyl)carbamoyl andrographolide;

14-[4'S,5R-(N-t-butoxycarbonyl-2',2'-dimethyl-4'-phenyl-5'-oxazolidine]carbonyl 3,19-isopropylidene andrographolide;

14-[4'S,5'R-(N-t-butoxycarbonyl-2',2'-dimethyl-4'-phenyl-5'-oxazolidine]carbonyl andrographolide;

3,19-Isopropylidene-14-(N-Boc-glycinyl) andrographolide;

14-(N-Boc-glycinyl)andrographolide;

14-O-Ethyl-3,19-isopropylidene andrographolide;

14-O-Ethyl andrographolide;

14-O-Methyl-3,19-isopropylidene andrographolide;

14-O-Methyl andrographolide;

14-(3,4-Dimethoxy)cinnamoyl andrographolide;

19-Trityl andrographolide;

3-Acetyl-19-trityl andrographolide;

3,14-Diacetyl-19-trityl andrographolide and

7-Hydroxy-3,14,19-triacetyl andrographolide.

9. A process for the preparation of the compound of the formula (I)

(I)

where $R^1$, $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, aralkanoyl, aralkenoyl, heteroaralkanoyl, heteroalkenoyl, sulfonyl group or a group —(CO)—W—$R^5$ where W represents O, S or $NR^6$, wherein $R^6$ represents hydrogen or substituted or unsubstituted ($C_1$–$C_6$)alkyl group, $R^5$ represents substituted or unsubstituted groups selected from alkyl, aryl, aralkyl or aroyl or $OR^2$ and $OR^3$ together form a substituted or unsubstituted cyclic 6 or 7 membered cyclic structure containing carbon and oxygen atoms and $R^4$ represents hydrogen; with provisos that (i) $R^1$, $R^2$ and $R^3$ may be same except when they represent hydrogen or alkanoyl group, (ii) when $R^2$ and $R^3$ represent hydrogen, $R^1$ does not represent unsubstituted alkanoyl; its stereoisomers, its polymorphs, its salts and its solvates, which the steps of comprises:

(a) reacting the compound of formula (VII)

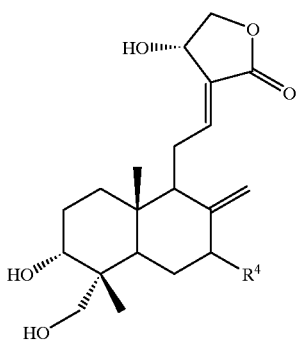

(VII)

with $R^1$-L, $R^2$-L and $R^3$-L, where $R^1$, $R^2$ and $R^3$ are as defined above and L is hydroxy, halogen, p-toluenesulfonate, methanesulfonate or trifluoromethanesulfonate; or alkanoate group to produce a compound of formula (I), where all symbols are as defined above and $R^4$ represents hydrogen or (b)(i) protecting the hydroxy groups present on carbons 3 or 19 or 3 and 19 together in the compound of formula (VII) with suitable protecting groups to produce a compound of formula (VIII),

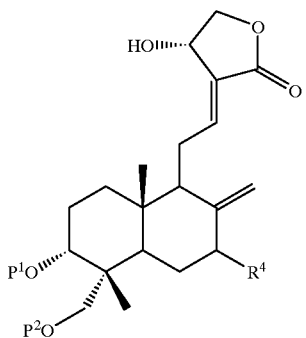

(VIII)

where $R^4$ represents hydrogen; $P^1$ and $P^2$ are same or different and represent hydrogen, trityl, t-butyl dimethyl silyl or pivaloyl; or esters; or $P^1$ and P together form methylene dioxy, isopropylidene, benzylidene, 1-phenyl ethylidene or carbonate, (ii) reacting the compound of formula (VIII) defined above with a compound of formula (IX)

$R^1$—L      (IX)

where $R^1$ and L are as defined above to produce a compound of formula (X),

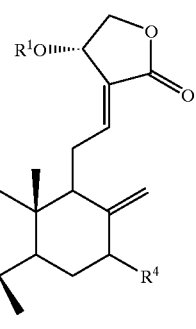

(X)

where $R^1$, $R^4$, $P^1$ and $P^2$ are as defined above, (iii) deprotecting the compound of formula (X) to produce a compound of formula (XI),

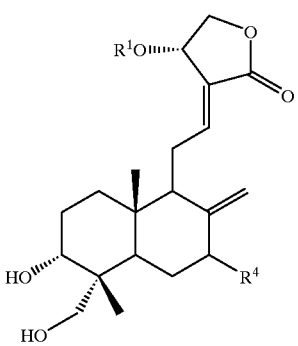

(XI)

where $R^1$ and $R^4$ are as defined above, (iv) reacting the compound of formula (XI) where $R^1$ has the meaning given above with $R^2$—L and/or $R^3$—L, where $R^2$ and $R^3$ are as defined above to produce a compound of formula (I), and if desired, (v) converting the compound of formula (I) into its stereoisomers, or pharmaceutical salts.

10. A compound of formula (X)

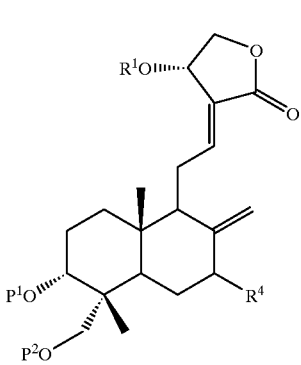

(X)

where $R^1$ represents hydrogen or substituted or unsubstituted groups selected from alkyl, aryl, heteroaryl, aralkyl, heteroaralkyl, alkanoyl, alkenoyl, aroyl, aralkanoyl, aralkenoyl, heteroaroyl, heteroaralkanoyl, heteroaralkenoyl, sulfonyl groups or a group —(CO)—W—$R^5$ where W represents O, S or $NR^6$, wherein $R^6$ represents hydrogen or substituted or unsubstituted ($C_1$–$C_6$)alkyl group, $R^5$ represents substituted or unsubstituted groups selected from alkyl, aryl, aralkyl or aroyl; $R^4$ represents hydrogen; $P^1$ and $P^2$ are same or different and independently represent trityl, t-butyldimethylsilyl or pivaloyl; or esters; or $P^1$ and $P^2$ together represent methylene dioxy, isopropylidene, benzylidene, 1-phenyl ethylidene or carbonate, its stereoisomers, its polymorphs, its salts and its solvates.

11. A process for the preparation of the compound of formula (X), as defined in claim 10

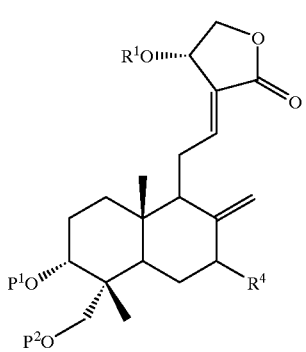

(X)

its stereoisomers, its polymorphs, its salts or its solvates which comprises the steps of:

(i) protecting the hydroxy groups present on carbons 3 or 19 or 3 and 19 together in the compound of formula (VII) with protecting groups to produce a compound of formula (VIII),

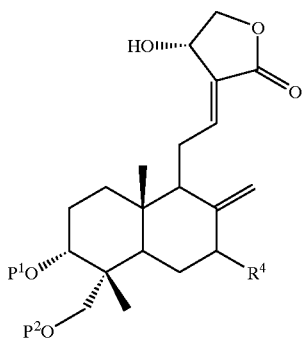

(VIII)

where $R^4$ represents hydrogen; $P^1$ and $P^2$ are same or different and represent hydrogen, trityl, t-butyl dimethyl silyl or pivaloyl; or esters; or $P^1$ and $P^2$ together form methylene dioxy, isopropylidene, benzylidene, 1-phenyl ethylidene or carbonate, (ii) reacting the compound of formula (VIII) defined above with compound of formula (IX)

$R^1$—L  (IX)

where $R^1$ is as defined in claim 10 and L is hydroxy, halogen, p-toluenesulfonate, methanesulfonate or trifluoromethanesulfonate; or alkanoate group to produce a compound of formula (X),

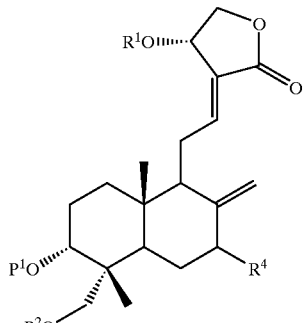

(X)

where $R^1$, $R^4$, $P^1$ and $P^2$ are as defined above.

12. A compound of formula (XI),

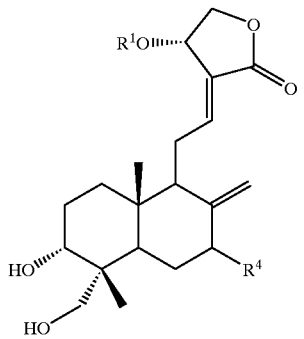

(XI)

where $R^1$ represents hydrogen or substituted or unsubstituted groups selected from alkyl, aryl, heteroaryl, aralkyl, heteroaralkyl, alkanoyl, alkenoyl, aroyl, aralkanoyl, aralkenoyl, heteroaroyl, heteroaralkanoyl, heteroaralkenoyl, sulfonyl groups or a group —(CO)—W—$R^5$ where W represents O, S or $NR^6$, wherein $R^6$ represents hydrogen or substituted or unsubstituted ($C_1$–$C_6$)alkyl group, $R^5$ represents substituted or unsubstituted groups selected from alkyl, aryl, aralkyl or aroyl and $R^4$ represents hydrogen, its stereoisomers, its polymorphs, its salts and its acceptable solvates.

13. A process for the preparation of the compound of formula (XI),

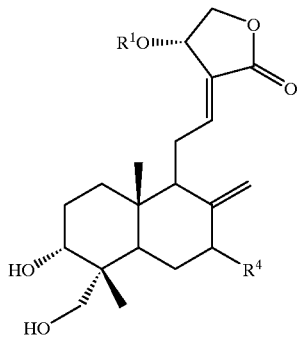

(XI)

as defined in claim 12, its stereoisomers, its polymorphs, its salts or its solvates, which the steps of comprises:

(i) protecting the hydroxy groups present on carbons 3 or 19 or 3 and 19 together in the compound of formula (VII) with a protecting group to produce a compound of formula (VIII), (VIII)

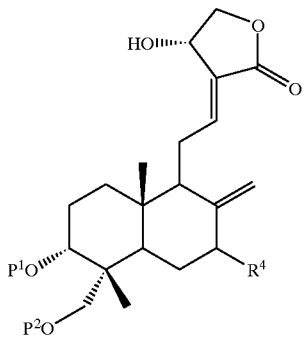

where $R^4$ represents hydrogen; $P^1$ and $P^2$ are same or different and represent hydrogen, trityl, t-butyl dimethyl silyl or pivaloyl; or esters; or $P^1$ and $P^2$ together form methylene dioxy, isopropylidene, benzylidene, 1-phenyl ethylidene or carbonate, (ii) reacting the compound of formula (VIII) defined above with compound of formula (IX)

$R^1$—L  (IX)

where L is hydroxy, halogen, p-toluenesulfonate, methanesulfonate or trifluoromethanesulfonate; or alkanoate group, and $R^1$ is as defined in claim 12 above to produce a compound of formula (X), (X)

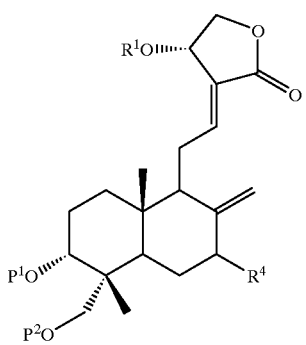

where $R^1$, $R^4$, $P^1$ and $P^2$ are as defined above, (iii) deprotecting the compound of formula (X) to produce a compound of formula (XI), (XI)

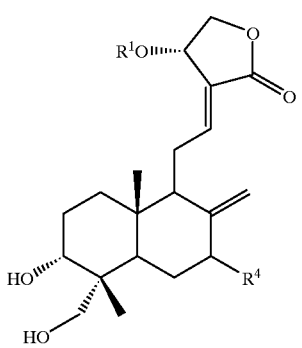

where $R^1$ and $R^4$ are as defined above.

14. A composition, which comprises a compound of formula (I), (I)

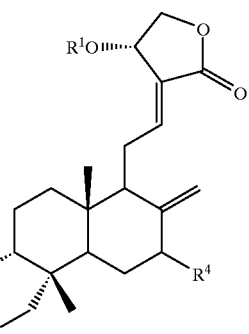

as defined in claim 1, and a pharmaceutically acceptable carrier, diluent, excipient or solvate.

15. The composition as claimed in claim 14, in the form of a tablet, capsule, powder, syrup, solution or suspension.

16. A method for treating psoriasis, HSV infections, HIV infections, restenosis, atherosclerosis, viral infections, malaria, bacterial infections, immunomodulation, liver disorders, cardiovascular disorders, diabetes, dyslipidemia, or other metabolic disorders, which comprises administering an effective amount of a compound of formula (I) as claimed in claim 1, to a patient in need thereof.

17. A method for treating insulin resistance, type II diabetes, leptin resistance, impaired glucose tolerance, dyslipidemia, body weight reduction, or disorders related to syndrome X which comprises administering an effective amount of a compound of formula (I) as claimed in claim 1 to a patient in need thereof.

18. The method according to claim 17, wherein the disorders relating to syndrome X are hypertension, obesity, insulin resistance, coronary heart disease and other cardiovascular disorders.

19. A method for preventing insulin resistance, type II diabetes, leptin resistance, impaired glucose tolerance, dyslipidemia, body weight reduction, or disorders related to syndrome X which comprises administering an effective amount of a compound of formula (I) as claimed in claim 1 to a patient in need thereof.

20. The method according to claim 19, wherein the disorders relating to syndrome X are hypertension, obesity, insulin resistance, coronary heart disease and other cardiovascular disorders.

21. A method for preventing psoriasis, restenosis, atherosclerosis, malaria, immunomodulation, liver disorders, cardiovascular disorders, diabetes, dyslipidemia, and other metabolic disorders, which comprises administering an effective amount of a compound of formula (I) as claimed in claim 1 to a patient in need thereof.

22. A composition which comprises a compound as defined in claim 8, and a pharmaceutically acceptable carrier, diluent, excipient or solvate.

23. The composition as claimed in claim 22, in the form of a tablet, capsule, powder, syrup, solution or suspension.

24. A method for treating insulin resistance, type II diabetes, leptin resistance, impaired glucose tolerance, dyslipidemia, body weight reduction, or disorders related to syndrome X which comprises administering an effective amount of a compound as claimed in claim 8 to a patient in need thereof.

25. The method according to claim 24, wherein the disorders relating to syndrome X are hypertension, obesity, insulin resistance, coronary heart disease and other cardiovascular disorders.

26. A method for preventing insulin resistance, type II diabetes, leptin resistance, impaired glucose tolerance, dyslipidemia, body weight reduction, or disorders related to syndrome X which comprises administering an effective amount of acompound as claimed in claim 8 to a patient in need thereof.

27. The method according to claim 26, wherein the disorders relating to syndrome X are hypertension, obesity, insulin resistance, coronary heart disease and other cardiovascular disorders.

28. A method for treating psoriasis, HSV infections, HIV infections, restenosis, atherosclerosis, viral infections, malaria, bacterial infections, immunomodulation, liver disorders, cardiovascular disorders, diabetes, dyslipidemia, or other metabolic disorders, which comprises administering an effective amount of a compound as claimed in claim 8, to a patient in need thereof.

29. A method for preventing psoriasis, restenosis, atherosclerosis, malaria, bacterial infections, immunomodulation, liver disorders, cardiovascular disorders, diabetes, dyslipidemia, and other metabolic disorders, which comprises administering an effective amount of a compound as claimed in claim 8, to a patient in need thereof.

30. A process for the preparation of the compound of formula (I),

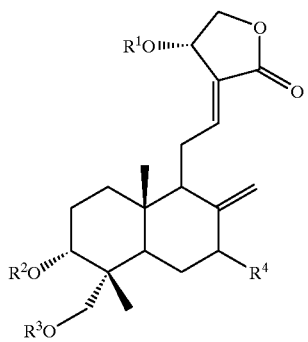

(I)

where $R^1$, $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, aralkanoyl, aralkenoyl, heteroaralkanoyl, heteroaralkenoyl, sulfonyl group or a group —(CO)—W—$R^5$ where W represents O, S or $NR^6$, wherein $R^6$ represents hydrogen or substituted or unsubstituted ($C_1$-$C_6$)alkyl group, $R^5$ represents substituted or unsubstituted groups selected from alkyl, aryl, aralkyl or aroyl or $OR^2$ and $OR^3$ together form a substituted or unsubstituted 6 or 7 membered cyclic structure containing carbon and oxygen atoms; $R^4$ represents hydrogen, halogen or $XR^7$ where X represents O, S, or NH and $R^7$ represents hydrogen or substituted or unsubstituted groups selected from alkyl, aryl, aralkyl, alkenoyl, alkanoyl, aroyl, heteroaroyl, aralkenoyl, aralkanoyl, sulfonyl groups or a group —(CO)—NH—$R^8$ where $R^8$ represents substituted or unsubstituted groups selected from alkyl, aryl, aralkyl; with provisos that (i) $R^1$, $R^2$ and $R^3$ may be same except when they represent hydrogen or alkanoyl group and (ii) when $R^2$ and $R^3$ represent hydrogen, $R^1$ does not represent unsubstituted alkanoyl; its stereoisomers, its polymorphs, its salts and its pharmaceutically acceptable solvates, which comprises the steps of:

(i) converting the compound of formula (I) where $R^4$ represents hydrogen and all other symbols are as defined earlier to produce a compound of formula (XII),

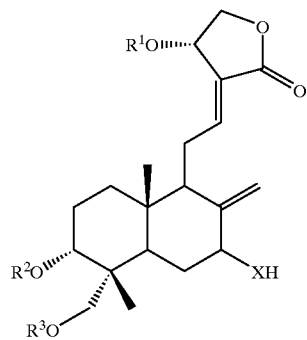

(XII)

where all the symbols are as defined above, the compound of formula (XII) represents a compound of formula (I) when X represents 0, and (ii) reacting the compound of formula (XII) with $R^7$—L where $R^7$ is as defined above, and L is hydroxy, halogen, p-toluenesulfonate, methanesulfonate or trifluoromethanesulfonate; or alkanoate group to produce a compound of formula (I).

31. A process for the preparation of the compound of formula (I),

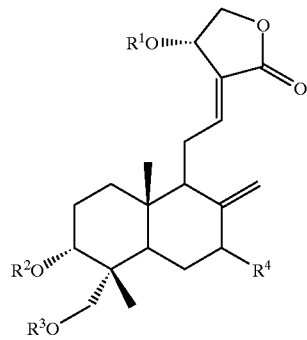

(I)

where $R^4$ represents halogen and $R^1$, $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, aralkanoyl, aralkenoyl, heteroaralkanoyl, heteroaralkenoyl, sulfonyl group or a group —(CO)—W— $R^5$ where W represents O, S or $NR^6$, wherein $R^6$ represents hydrogen or substituted or unsubstituted ($C_1$-$C_6$)alkyl group, $R^5$ represents substituted or unsubstituted groups selected from alkyl, aryl, aralkyl or aroyl or $OR^2$ and $OR^3$ together form a substituted or unsubstituted 6 or 7 membered cyclic structure containing carbon and oxygen atoms; $R^4$ represents halogen, with provisos that (i) $R^1$, $R^2$ and $R^3$ may be same except when they represent hydrogen or alkanoyl group and (ii) when $R^2$ and $R^3$ represent hydrogen, $R^1$ does not represent unsubstituted alkanoyl; its stereoisomers, its polymorphs, its pharmaceutically acceptable salts and its pharmaceutically acceptable solvates, which comprises the steps of:

(a)(i) converting the compound of formula (I) where $R^4$ represents hydrogen and all other symbols are as defined above to produce a compound of formula (XII),

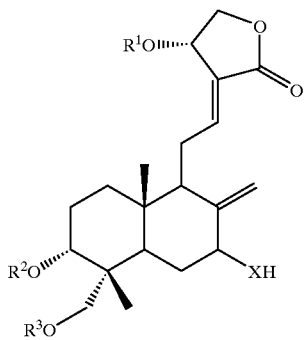

(XII)

where all the symbols are as defined above, the compound of formula (XII) represents a compound of formula (I) when X represents O, (ii) converting the compound of formula (XII) to a compound of formula (I), where $R^4$ represents halogen atom or (b) reacting the compound of formula (I) where $R^4$ represents hydrogen and all other symbols are as defined earlier with a halogenating agent to produce a compound of formula (I), where $R^4$ represents halogen atom.

32. The compound according to claim 3, wherein when the substituents on $R^1$, $R^2$, $R^3$, $R^7$ and $R^8$ are substituted, the substituent is selected from halogen, hydroxy, nitro, cyano, amino, ($C_1$-$C_6$)alkyl, aryl or ($C_1$-$C_6$)alkoxy groups.

33. A composition, which comprises a compound of formula (X),

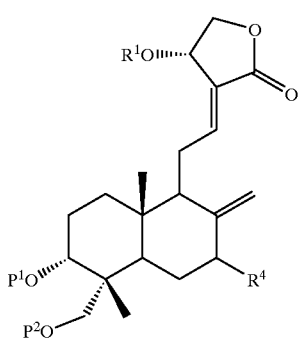

(X)

as defined in claim 10, and a pharmaceutically acceptable carrier, diluent, excipient or solvate.

34. The composition as claimed in claim 33, in the form of a tablet, capsule, powder, syrup, solution or suspension.

35. A method for treating psoriasis, HSV infections, HIV infections, restenosis, atherosclerosis, viral infections, malaria, bacterial infections, immunomodulation, liver disorders, cardiovascular disorders, diabetes, dyslipidemia, or other metabolic disorders, which comprises administering an effective amount of a compound of formula (I) as claimed in claim 10, to a patient in need thereof.

36. A method for treating insulin resistance, type II diabetes, leptin resistance, impaired glucose tolerance, dyslipidemia, body weight reduction, or disorders related to syndrome X which comprises administering an effective amount of a compound of formula (X) as claimed in claim 10 to a patient in need thereof.

37. The method according to claim 36, wherein the disorders relating to syndrome X are hypertension, obesity, insulin resistance, coronary heart disease and other cardiovascular disorders.

38. A method for preventing insulin resistance, type II diabetes, leptin resistance, impaired glucose tolerance, dyslipidemia, body weight reduction, or disorders related to syndrome X which comprises administering an effective amount of a compound of formula (X) as claimed in claim 10 to a patient in need thereof.

39. The method according to claim 38, wherein the disorders relating to syndrome X are hypertension, obesity, insulin resistance, coronary heart disease and other cardiovascular disorders.

40. A method of preventing psoriasis, restenosis, atherosclerosis, malaria, immunomodulation, liver disorders, cardiovascular disorders, diabetes, dyslipidemia, and other metabolic disorders, which comprises administering an effective amount of a compound of formula (X) as claimed in claim 10 to a patient in need thereof.

41. A composition which comprises a compound or formula (XI) as defined in claim 12, and a pharmaceutically acceptable carrier, diluent, excipient or solvate.

42. The composition as claimed in claim 41, in the form of a tablet, capsule, powder, syrup, solution or suspension.

43. A method for treating insulin resistance, type II diabetes, leptin resistance, impaired glucose tolerance, dyslipidemia, body weight reduction, and disorders related to syndrome X which comprises administering an effective amount of a compound as claimed in claim 12 to a patient in need thereof.

44. The method according to claim 43, wherein the disorders relating to syndrome X are hypertension, obesity, insulin resistance, coronary heart disease and other cardiovascular disorders.

45. A method for preventing insulin resistance, type II diabetes, leptin resistance, impaired glucose tolerance, dyslipidemia, body weight reduction, and disorders related to syndrome X which comprises administering an effective amount of a compound as claimed in claim 12 to a patient in need thereof.

46. The method according to claim 45, wherein the disorders relating to syndrome X are hypertension, obesity, insulin resistance, coronary heart disease and other cardiovascular disorders.

47. A method for treating psoriasis, HSV infections, HIV infections, restenosis, atherosclerosis, viral infections, malaria, bacterial infections, immunomodulation, liver disorders, cardiovascular disorders, diabetes, dyslipidemia, and other metabolic disorders, which comprises administering an effective amount of a compound as claimed in claim 12, to a patient in need thereof.

48. A method for preventing psoriasis, restenosis, atherosclerosis, malaria, bacterial infections, immunomodulation, liver disorders, cardiovascular disorders, diabetes, dyslipidemia, and other metabolic disorders, which comprises administering an effective amount of a compound as claimed in claim 12, to a patient in need thereof.

49. The compound according to claim 2, wherein the substituents on $R^9$ and $R^{10}$ are selected from hydroxy, halogen, nitro, cyano, amino, $(C_1-C_6)$alkyl, $(C_1-C_6)$alkoxy, aryl or aroyl groups.

50. A method for treating breast, colon, lung, ovarian, prostate or renal cancer or cancer of the central nervous system or melanoma, which comprises administering an effective amount of a compound of formula (I) as claimed in claim 1, to a patient in need thereof.

51. A method for treating breast, colon, lung, ovarian, prostate or renal cancer or cancer of the central nervous system or melanoma, which comprises administering an effective amount of a compound of formula (I) as claimed in claim 8 to a patient in need thereof.

52. A method for treating breast, colon, lung, ovarian, prostate or renal cancer or cancer of the central nervous system or melanoma, which comprises administering an effective amount of a compound of formula (I) as claimed in claim 10, to a patient in need thereof.

53. A method for treating breast, colon, lung, ovarian, prostate or renal cancer or cancer of the central nervous system or melanoma, which comprises administering an effective amount of a compound of formula (I) as claimed in claim 12, to a patient in need thereof.

* * * * *